US012636103B2

(12) United States Patent
Morley et al.

(10) Patent No.: US 12,636,103 B2
(45) Date of Patent: May 26, 2026

(54) PATIENT-SPECIFIC REMOTE CENTER OF MOTION FOR ROBOTIC SURGICAL SYSTEM

(71) Applicant: Cilag GmbH International, Zug (CH)

(72) Inventors: Tracey A. Morley, Sunnyvale, CA (US); Rudolph H. Nobis, Mason, OH (US); Andrew Jernberg, San Francisco, CA (US); Mario F. Luces Rosado, Oakland, CA (US); Dillon R. Carey, Mountain View, CA (US); Matthew T. Hill, Norwood, OH (US); Chelsea Chen, Palo Alto, CA (US)

(73) Assignee: Cilag GmbH International, Zug (CH)

( * ) Notice: Subject to any disclaimer, the term of this patent is extended or adjusted under 35 U.S.C. 154(b) by 122 days.

(21) Appl. No.: 18/340,947

(22) Filed: Jun. 26, 2023

(65) Prior Publication Data

US 2024/0423732 A1     Dec. 26, 2024

(51) Int. Cl.
| | |
|---|---|
| *A61B 34/35* | (2016.01) |
| *A61B 34/00* | (2016.01) |
| *A61B 34/20* | (2016.01) |
| *A61B 34/30* | (2016.01) |

(52) U.S. Cl.
CPC .............. *A61B 34/35* (2016.02); *A61B 34/20* (2016.02); *A61B 34/76* (2016.02); *A61B 2034/2055* (2016.02); *A61B 2034/2059* (2016.02); *A61B 34/30* (2016.02); *A61B 2034/301* (2016.02); *A61B 2034/305* (2016.02)

(58) Field of Classification Search
CPC ......... A61B 34/35; A61B 34/20; A61B 34/76; A61B 2034/2055; A61B 2034/2059; A61B 2034/301; A61B 2034/305; A61B 34/37; A61B 2017/00477; A61B 2017/00557; A61B 2090/061; A61B 17/4241; A61B 2090/065; A61B 2090/306; A61B 2090/309; A61B 2090/376
See application file for complete search history.

(56) References Cited

U.S. PATENT DOCUMENTS

| | | |
|---|---|---|
| 9,743,955 B2 | 8/2017 | Hill et al. |
| 9,763,741 B2 | 9/2017 | Alvarez et al. |
| 9,788,859 B2 | 10/2017 | Parys |
| 10,166,082 B1 | 1/2019 | Hariri et al. |

(Continued)

*Primary Examiner* — Michael C Zarroli
(74) *Attorney, Agent, or Firm* — FBT Gibbons LLP

(57) ABSTRACT

An apparatus includes a robotic coupling base configured to selectively coupled with a robotic arm of a robotic surgical system. A shaft extends distally from the robotic coupling base. The shaft includes a distal portion dimensioned to be inserted into a naturally occurring orifice of a patient. A remote center of motion (RCM) measuring feature is associated with the robotic coupling base or the shaft, the RCM measuring feature being configured to communicate with the robotic surgical system while the robotic coupling based is selectively coupled with the robotic arm. The RCM measuring feature is configured to measure a distance between an entry point of the naturally occurring orifice of the patient and a predetermined location of the apparatus. The RCM measuring feature is further configured to communicate the distance to the robotic surgical system.

20 Claims, 29 Drawing Sheets

(56)  References Cited

U.S. PATENT DOCUMENTS

| | | | |
|---|---|---|---|
| 10,464,209 B2 | 11/2019 | Ho et al. | |
| 10,639,072 B2 | 5/2020 | Ahluwalia | |
| 10,667,875 B2 | 6/2020 | DeFonzo et al. | |
| 10,765,303 B2 | 9/2020 | Graetzel et al. | |
| 10,827,913 B2 | 11/2020 | Ummalaneni et al. | |
| 10,881,280 B2 | 1/2021 | Baez, Jr. | |
| 10,898,277 B2 | 1/2021 | Srinivasan et al. | |
| 11,058,493 B2 | 7/2021 | Rafii-Tari et al. | |
| 11,090,082 B2 | 8/2021 | Weihe et al. | |
| 2021/0100584 A1 | 4/2021 | Einarsson | |
| 2023/0074350 A1* | 3/2023 | Scheib .................. | A61B 34/30 |
| 2023/0293254 A1* | 9/2023 | Sarli ...................... | A61G 13/04 |
| | | | 700/245 |

* cited by examiner

CONTROL CONSOLE

PATIENT-SPECIFIC REMOTE CENTER OF MOTION FOR ROBOTIC SURGICAL SYSTEM

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

During a hysterectomy procedure, a colpotomy may be performed at the cervicovaginal junction. Such procedures may include the use of a uterine manipulator that includes a colpotomy cup or similar structure. Examples of instruments that may be used during a hysterectomy procedure are described in U.S. Pat. No. 9,743,955, entitled "Intracorporeal Transilluminator of Tissue Using LED Array," issued Aug. 29, 2017; U.S. Pat. No. 9,788,859, entitled "Uterine Manipulators and Related Components and Methods," issued Oct. 17, 2017; U.S. Pat. No. 10,639,072, entitled "Uterine Manipulator," issued May 5, 2020; U.S. Pat. No. 11,090,082, entitled "Colpotomy Systems, Devices, and Methods with Rotational Cutting," issued Aug. 17, 2021; and U.S. Pub. No. 2021/0100584, entitled "Uterine Manipulator," published Apr. 8, 2021, issued as U.S. Pat. No. 12,096,960, on Sep. 24, 2024.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview of Example of Robotic Surgical System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the clinician. Additionally, the system may provide the clinician with the ability to perform the procedure from an ergonomic position without the need for awkward arm motions and positions. Still further, the system may provide the clinician with the ability to perform the procedure with improved case of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Table

Figure 1:
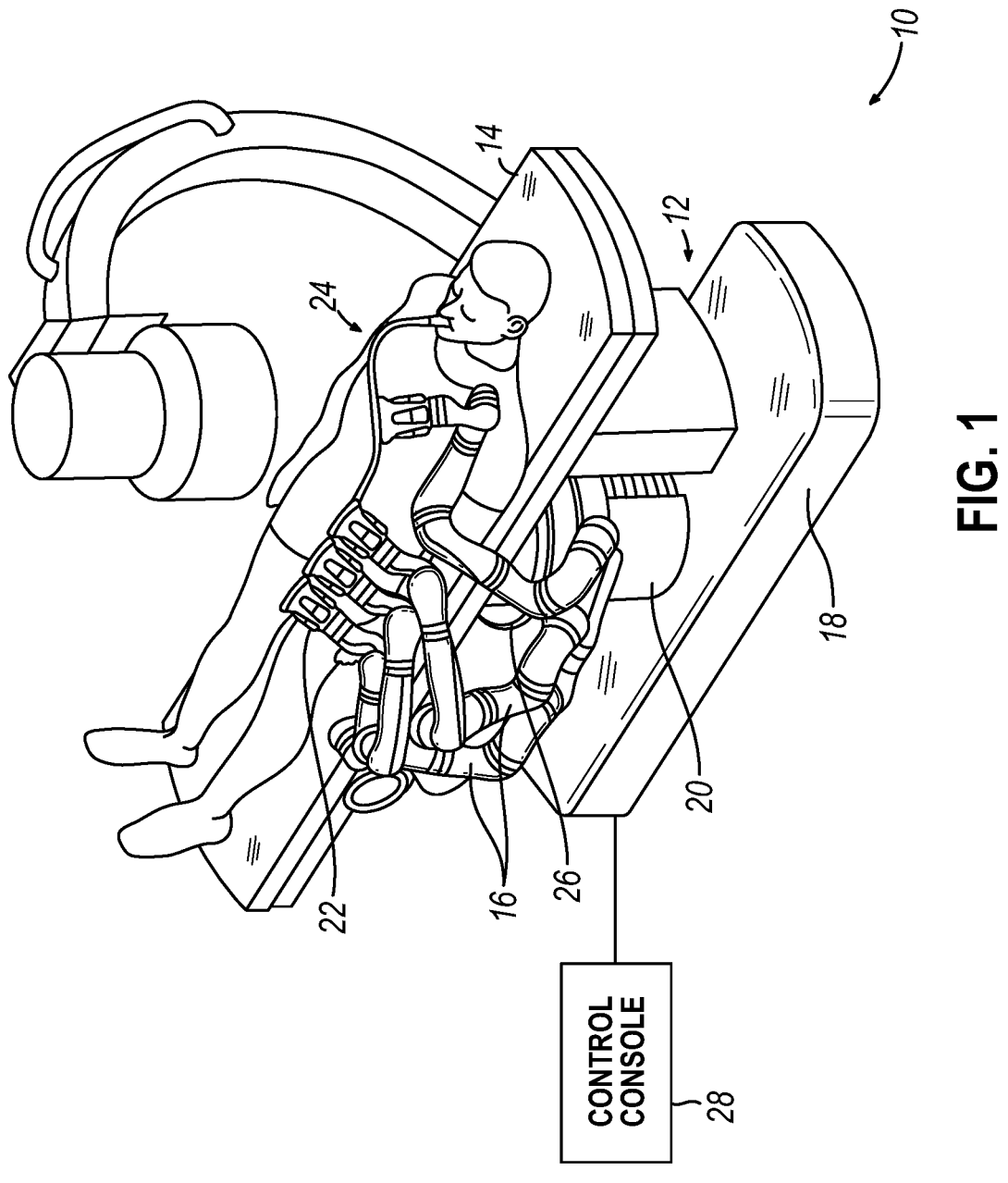
FIG. 1 depicts a perspective view of an example of a table-based robotic system that includes a control console and a plurality of robotic arms.

FIG. 1 illustrates an example of a robotic surgical system (10). Robotic surgical system (10) includes a support structure (12) for supporting a platform (14) (shown as a "table" or "bed") over the floor and one or more robotic arms (16). Support structure (12) includes a base (18) and a column (20). Column (20) structurally supports platform (14) and provides a path for vertical translation of the carriages. In some versions, a table base may stow and store robotic arms (16) when not in use. Column (20) of the present example also includes a ring-shaped carriage (26), from which robotic arms (16) are based. A control console (28) is coupled with robotic surgical system (10).

Robotic arms (16) are shown as part of a table-mounted system, but in other configurations, robotic arms (16) may be mounted in a cart, ceiling or sidewall, or other suitable support surface. Robotic arms (16) are shown as extending from column (20) via carriage (26). However, robotic arms (16) may be coupled with robotic surgical system (10) using a variety of suitable structures. While robotic arms (16) are all shown as being positioned on one side of the patient in FIG. 1, other configurations may position robotic arms (16) on both sides of the patient, between the legs of the patient, and/or in any other suitable locations. Tool drivers (22) are positioned at distal ends of robotic arms (16) in the present example. Tool drivers (22) are operable to manipulate one or more instruments (24), as will be described in greater detail below.

B. Example of a Robotic Arm, Tool Drive, and Tool

Figures 2, 3:
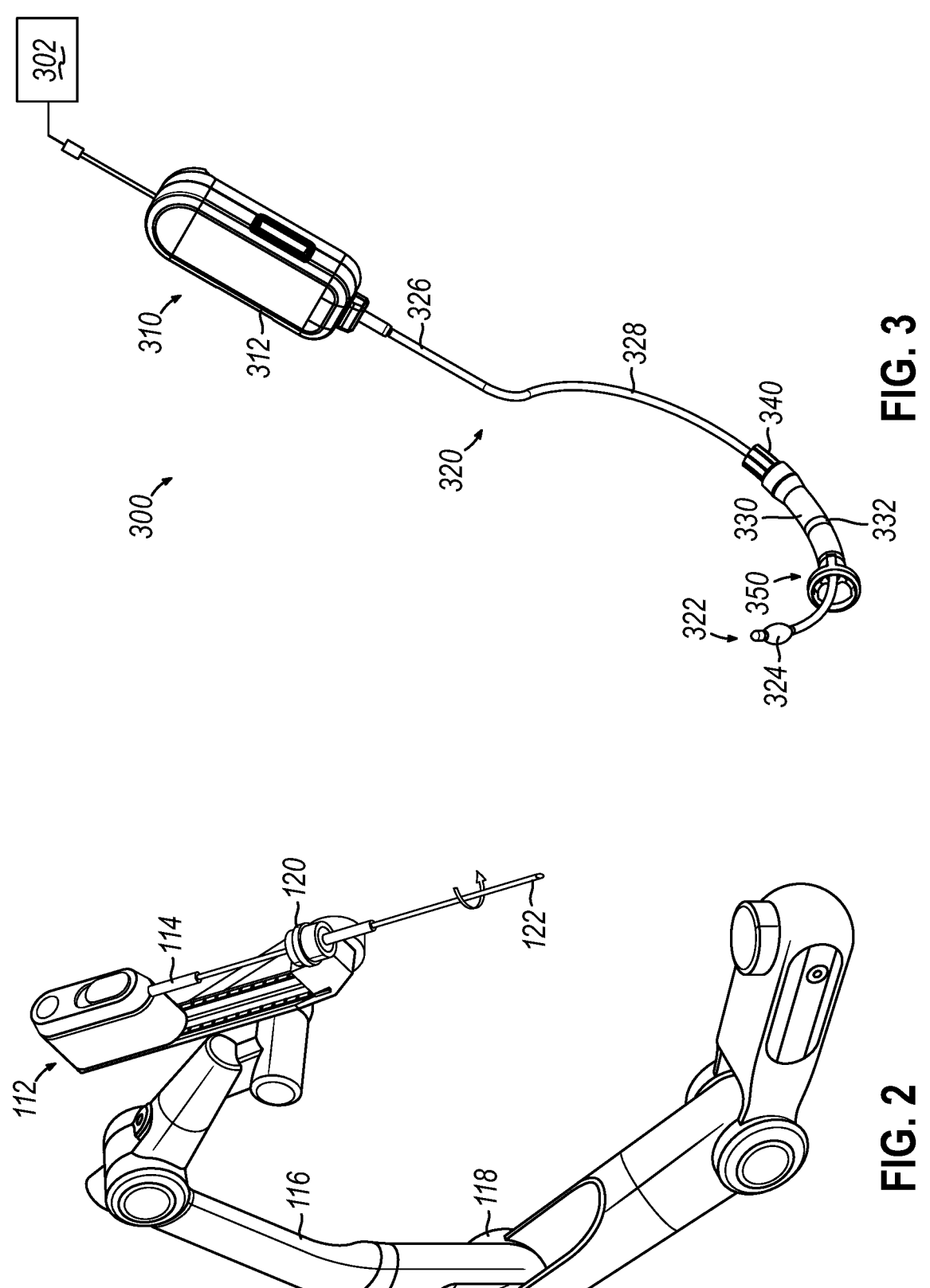
FIG. 2 depicts a perspective view of an example of a robotic arm, an example of a tool drive, and an example of an instrument, each configured for use with the table-based robotic system of FIG. 1.
FIG. 3 depicts a perspective view of an example of a uterine manipulator that may be operatively attached to the tool drive of FIG. 2.

FIG. 2 shows an example of a robotic arm (110), a tool driver (112), and an instrument (114), which may be incorporated into robotic surgical system (10) in place of a robotic arm (16), a tool driver (22), and an instrument (24) that are shown in FIG. 1. Additional examples of robotic arms, a tool drivers, and instruments are shown and described in U.S.

Pat. No. 10,166,082, entitled "System and Method for Controlling a Robotic Wrist," issued Jan. 1, 2019, the disclosure of which is incorporated by reference herein, in its entirety.

As shown in FIG. 2, robotic arm (110) includes a plurality of links (116) and a plurality of joints (118) for actuating links (116) relative to one another. Tool driver (112) is attached to the distal end of robotic arm (110). Tool driver (112) includes a cannula (120) coupled to the end of tool driver (112), to receive and guide instrument (114). Instrument (114) may include an endoscope, a laparoscope, a stapler, graspers, an ultrasonic instrument, an RF electrosurgical instrument, or any other suitable kind of instrument. Instrument (114) is inserted into the patient via cannula (120). The distal end of instrument (114) includes an end effector (122). End effector (122) is configured to interact with the patient (e.g., providing visualization, stapling, grasping, ultrasonic cutting and/or sealing, electrosurgical cutting and/or sealing, etc.).

Joints (118) of robotic arm (110) may be actuated to selectively position and orient tool driver (112), which actuates the end effector (122) for robotic surgeries. Joints (118) may include various types, such as a pitch joint or a roll joint, which may substantially constrain the movement of the adjacent links (116) around certain axes relative to other links (116). Each joint (118) represents an independent degree of freedom available to robotic arm (110). A multitude of joints (118) result in a multitude of degrees of freedom, allowing for "redundant" degrees of freedom. Redundant degrees of freedom allow the robotic arms (110) to position their respective end effectors (122) at a specific position, orientation, and trajectory in space using different positions links (116) and angles of joints (118). This allows for the system to position and direct an instrument (114) from a desired point in space while allowing the clinician to move joints (118) into a clinically advantageous position away from the patient to create greater access, while avoiding collisions of robotic arms (110).

II. Example of Robotically Controlled Uterine Manipulator

In some conventional hysterectomy procedures, a first clinician may serve in a role of forming incisions and performing other laparoscopic operations to remove the uterus of a patient, while a second clinician may serve in a role of manipulating the position and orientation of the uterus of the patient to facilitate the operations being performed by the first clinician. Such team-based procedures may require clear communication between the first clinician and the second clinician, with the first clinician instructing the second clinician on desired positioning and orientation of the uterus, and with the second clinician responding in a timely and accurate fashion. In some scenarios, such communications may break down or otherwise yield undesirable results, such as the second clinician not precisely positioning or orienting the uterus when and where the first clinician wishes. It may therefore be desirable to provide a robotic system that is capable of performing at least part of the role of the second clinician, such that the robotic system may at least partially control the position and orientation of the uterus based on the desire of the first clinician. Examples of how a robotic system may provide uterine manipulation are described in greater detail below. The following examples may be readily incorporated into robotic system (10)

described herein; or in any other suitable robotic system as would be apparent to one skilled in the art in view of the teachings herein.

FIG. 3 shows an example of a uterine manipulator (300) that may be secured to a robotic arm (100) shown in FIG. 2 in replacement of instrument (114). Uterine manipulator (300) may be removably coupled with tool driver (112) and/or cannula (120), such that robotic arm (110) may selectively position and orient uterine manipulator (300) in relation to a patient by driving robotic arm (110). As best seen in FIG. 3, uterine manipulator (300) of the present example includes a tool driver interface (310), a shaft (320), a sleeve (330), a sleeve locking ring (340), and a colpotomy cup (350). Tool driver interface (310) includes a base (312). Base (312) is configured to removably couple with tool driver (112) of robotic arm (110) to thereby secure uterine manipulator (300) with robotic arm (110).

A linear portion (326) of shaft (320) that extends distally from base (312) may extend through cannula (120) when uterine manipulator (300) is coupled to robotic arm (110). In some instances, linear portion (326) of shaft (320) slidably extends through cannula (120); while in other instances linear portion (326) of shaft (320) may be temporarily secured to cannula (120). By way of example only, base (312) and tool driver (112) may include complementary bayonet fitting features, complementary threading, complementary snap-fit features, and/or any other suitable kinds of structures to provide a removable coupling. Shaft (320) is configured to couple with a pressurized fluid source (302). Pressurized fluid source (302) may contain pressurized air, pressurized saline, or any other suitable kind of pressurized fluid. The pressurized fluid may be used to selectively inflate balloons (324, 332), which will be described in greater detail below.

Shaft (320) of the present example extends distally from base (312). Shaft (320) includes proximal linear portion (326) and distal curved portion (328). In some versions, shaft (320) is rigid. In some other versions, shaft (320) is flexible yet resiliently biased to assume the curved configuration shown. Any suitable biocompatible material(s) may be used to form shaft (320), including but not limited to metallic materials, plastic materials, and combinations thereof. An inflatable balloon (324) is positioned near distal end (322) of shaft (320). Balloon (324) may be formed of an extensible material or a non-extensible material. The interior of shaft (320) includes one or more lumen(s) that are configured to communicate pressurized fluid from pressurized fluid source (302) to balloon (324). While balloon (324) is positioned near distal end (322) of shaft (320) in the present example, other versions may include a different kind of expandable member. By way of example only, an alternative expandable member may include a mechanically expandable component such as an expandable mesh structure, an expanding umbrella-like structure, or any other suitable kind of expandable structure or assembly. In some versions, distal end (322) of shaft (320) may also include an illuminating element (e.g., one or more LEDs, a lens illuminated by one or more optical fibers, etc.). In such versions, one or more wires, optical fibers, and/or other components may extend along the length of shaft (320) to couple with a source of electrical power, a source of light, etc.

Figure 6A:
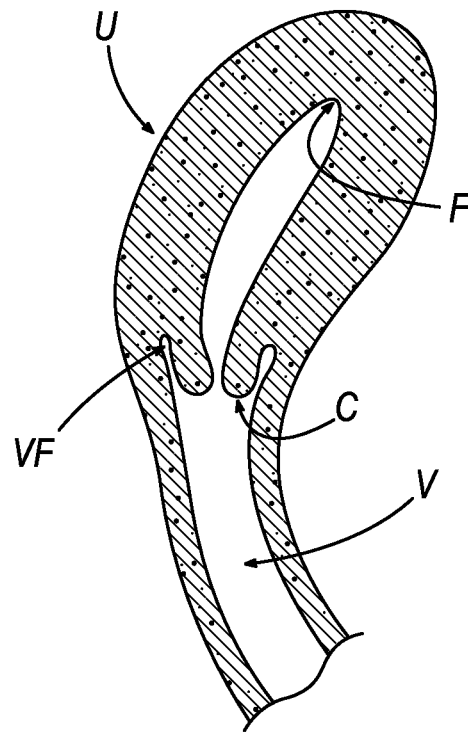
FIG. 6A depicts a mid-sagittal cross-sectional view of a vagina and uterus.
Figure 6B:
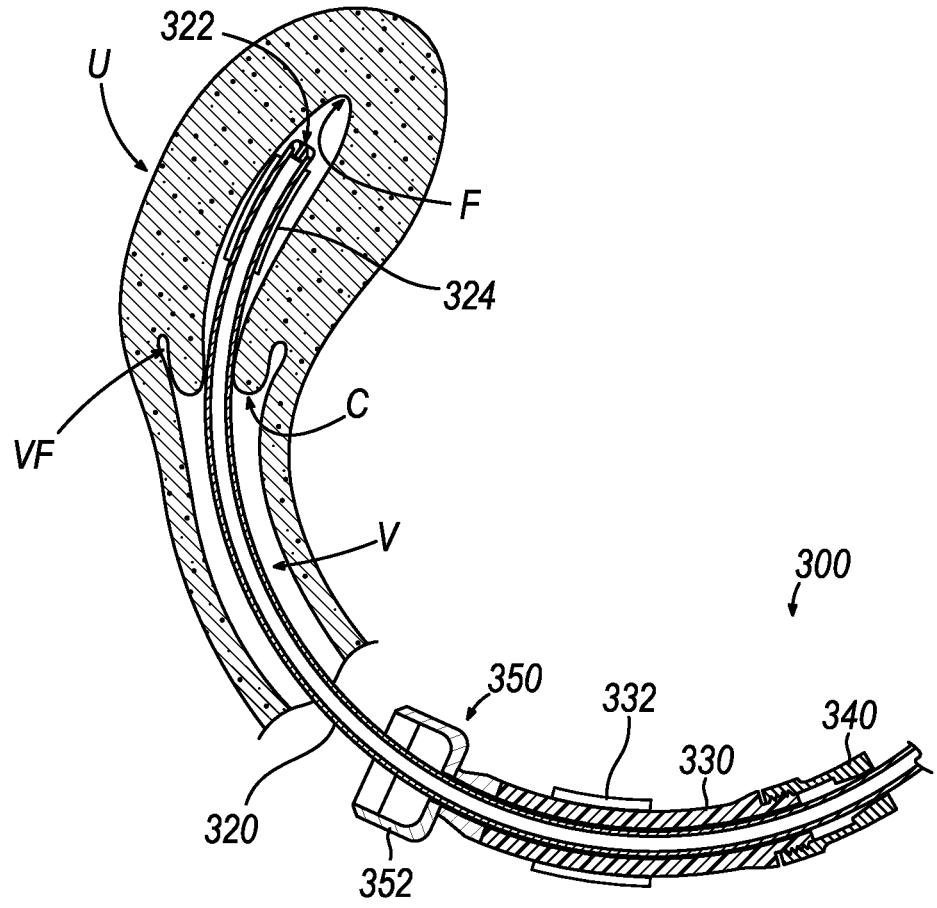
FIG. 6B depicts a mid-sagittal cross-sectional view of the vagina and uterus of FIG. 6A, with the shaft of the uterine manipulator instrument of FIG. 3 inserted through the vagina into the uterus, with a balloon of the uterine manipulator instrument in a deflated state, and with a sleeve of the uterine manipulator instrument in a proximal position.
Figure 6C:
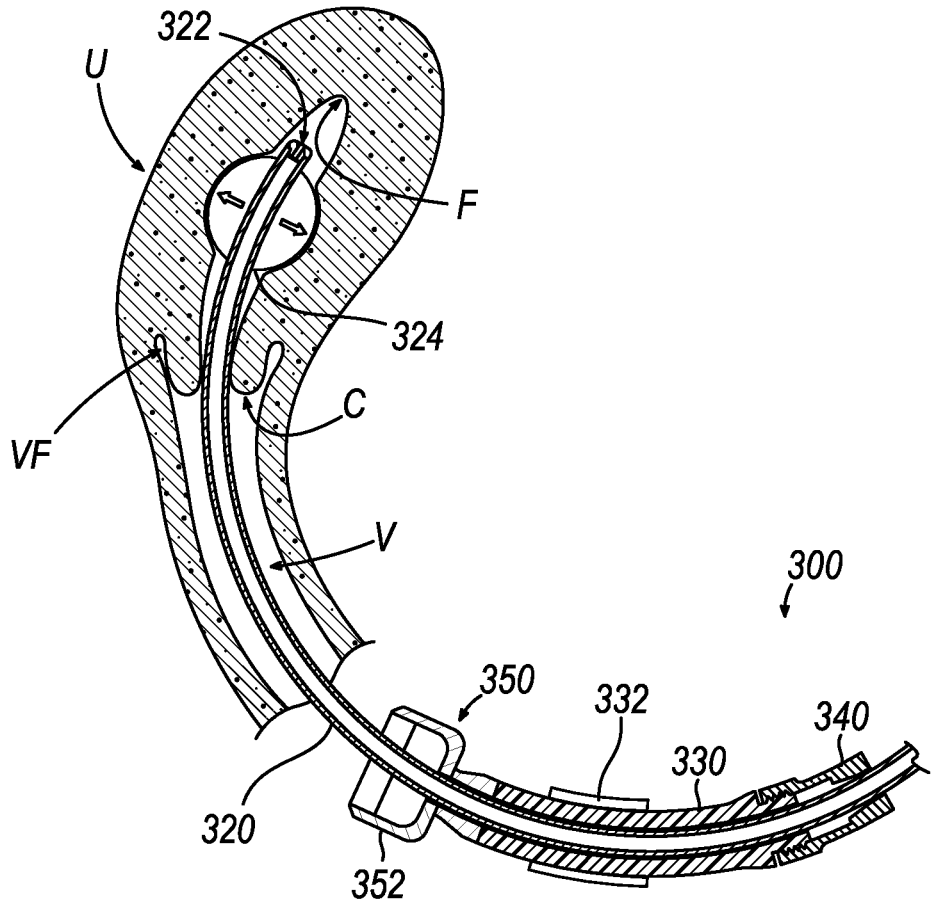
FIG. 6C depicts a mid-sagittal cross-sectional view of the vagina and uterus of FIG. 6A, with the shaft of the uterine manipulator instrument of FIG. 3 inserted through the vagina into the uterus, with the balloon of the uterine manipulator instrument in an inflated state, and with the sleeve of the uterine manipulator instrument in the proximal position.
Figure 6D:
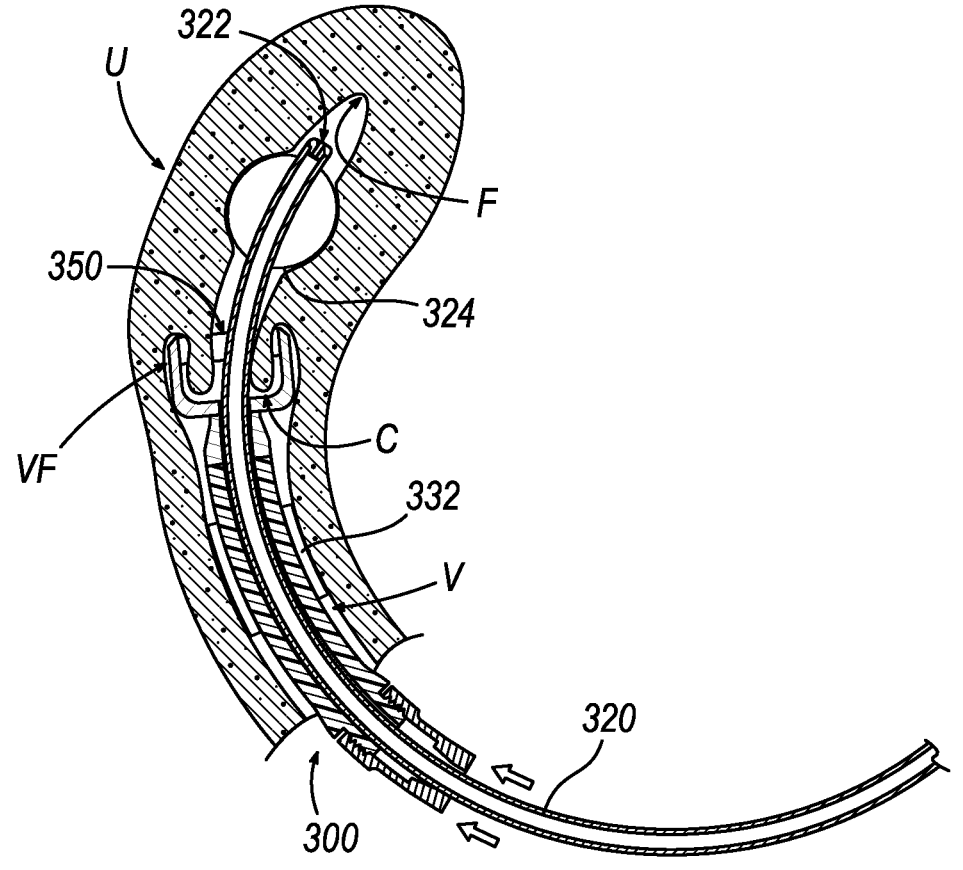
FIG. 6D depicts a mid-sagittal cross-sectional view of the vagina and uterus of FIG. 6A, with the shaft of the uterine manipulator instrument of FIG. 3 inserted through the vagina into the uterus, with the balloon of the uterine manipulator instrument in the inflated state, with the sleeve of the uterine manipulator instrument in a distal position such that the colpotomy cup of the sleeve is engaged with the cervix, and with a balloon of the sleeve in a deflated state.
Figure 6E:
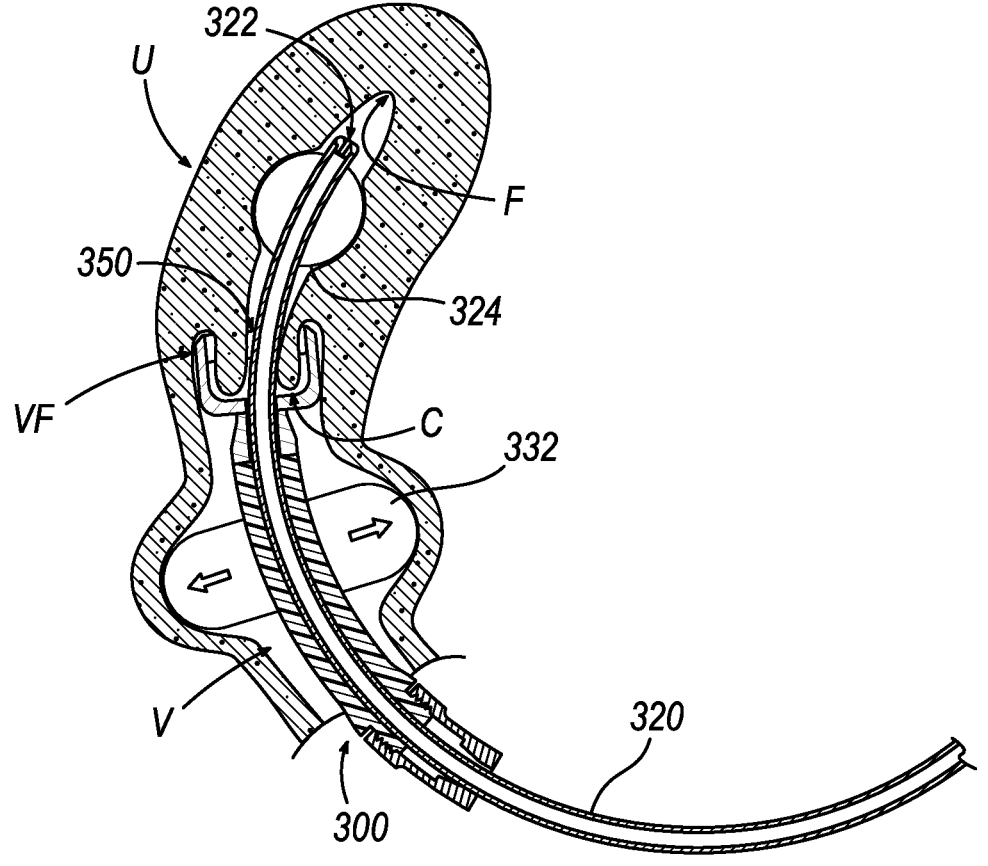
FIG. 6E depicts a mid-sagittal cross-sectional view of the vagina and uterus of FIG. 6A, with the shaft of the uterine manipulator instrument of FIG. 3 inserted through the vagina into the uterus, with the balloon of the uterine manipulator instrument in the inflated state, with the sleeve of the uterine manipulator instrument in the distal position such that the colpotomy cup of the sleeve is engaged with the cervix, and with the balloon of the sleeve in an inflated state.

Sleeve (330) is slidably coupled to distal curved portion (328) of shaft (320), such that sleeve (330) may slide along shaft (320) from a proximal position (FIGS. 6B-6C) to any number of distal positions (FIGS. 3, 6D-6E). Sleeve (330) is generally cylindraceous and rigid; and extends along a curved axis such that the curved profile complements the curved profile of curved portion (328) of shaft (320). Sleeve (330) may be formed of plastic, metal, and/or any other suitable biocompatible material(s), including combinations of materials. Locking ring (340) is rotatably secured to the proximal end of sleeve (330), while colpotomy cup (350) is fixedly secured to the distal end of sleeve (330). An inflatable balloon (332) is positioned along sleeve (330), between locking ring (340) and colpotomy cup (350). Balloon (332) may be formed of an extensible material or a non-extensible material. The interior of sleeve (330) includes one or more lumen(s) that are configured to communicate pressurized fluid from pressurized fluid source (302) to balloon (332). Such a lumen or lumens may be coupled with pressurized fluid source (302) via a flexible tube (not shown). In some versions, one or more lumens or tubes within shaft (320) provide at least part of the fluid pathway between balloon (332) and pressurized fluid source (302).

Locking ring (340) is operable to selectively secure the position of sleeve (330) along the length of shaft (320). For instance, locking ring (340) may be rotated to a first angular position relative to sleeve (330) to provide an unlocked state where sleeve (330) may be freely translated along shaft (320). Locking ring (340) may then be rotated to a second angular position relative to sleeve (330) to provide a locked state where the position of sleeve (330) along shaft (320) is secured until locking ring (340) is rotated back to the first angular position. By way of example only, locking ring (340) may include one or more frictional braking structures that selectively engage shaft (320) to thereby provide the locked state. Alternatively, locking ring (340) may selectively engage shaft (320) in any other suitable fashion.

Figure 4:
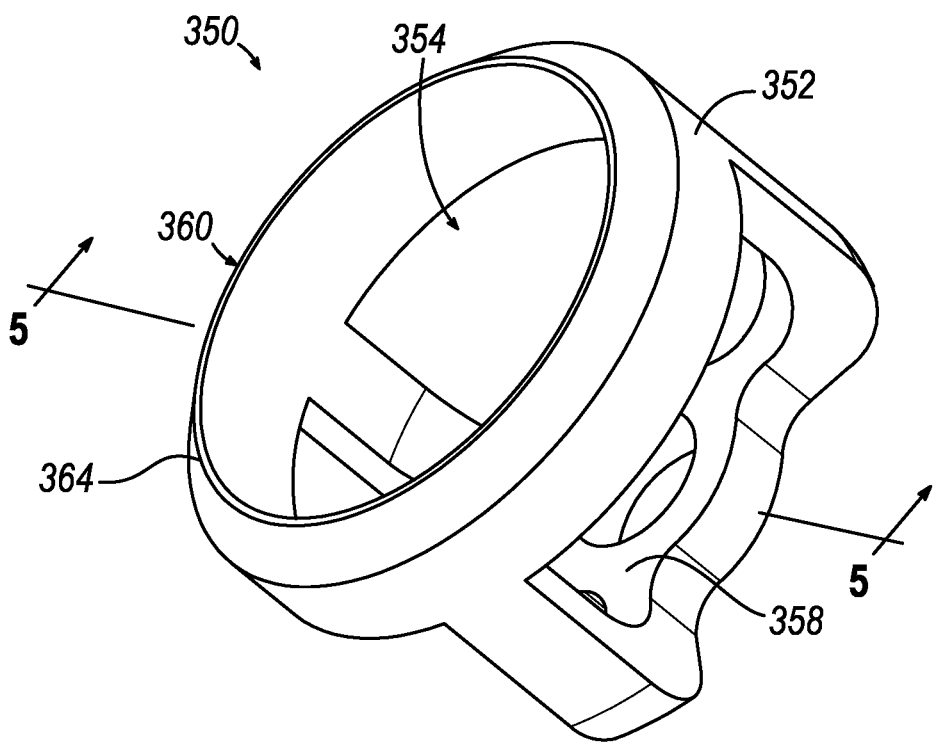
FIG. 4 depicts a perspective view of a colpotomy cup of the uterine manipulator of FIG. 3.
Figure 5:
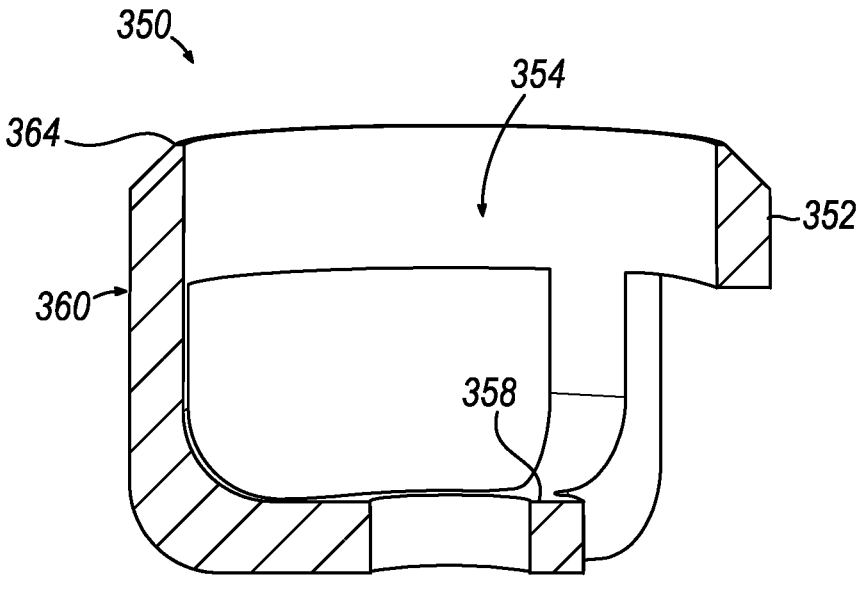
FIG. 5 depicts a cross-sectional view of the colpotomy cup of FIG. 4, taken along line 5-5 of FIG. 4.

FIGS. 4-5 show colpotomy cup (350) in greater detail. As shown, colpotomy cup (350) of the present example includes a body (352) defining an interior space (354). Body (352) further includes a floor (358) at the bottom of interior space (354) and an open distal end (360). A plurality of lateral openings (356) are in communication with interior space (354). Distal end (360) includes a distally presented annular edge (364). Colpotomy cup (350) may be formed of plastic, metal, and/or any other suitable biocompatible material(s), including combinations of materials.

FIGS. 6A-6E show an example of a procedure in which uterine manipulator (300) is used. As shown in FIG. 6A, the anatomical context in which uterine manipulator (300) is used includes a vagina (V) and uterus (U) of a patient. As shown in FIG. 6B, distal end (322) of shaft (320) is inserted through the vagina (V) and into the uterus (U) via the cervix (C), while sleeve (330) is in a proximal position along shaft (320). Balloon (324) is in a deflated state during this stage of insertion. In some versions, uterine manipulator (300) is fully decoupled from robotic arm (110) during the process leading up to the stage shown in FIG. 6B, such that uterine manipulator (300) is advanced to this state manually by a human operator grasping a proximal portion of uterine manipulator (300) (e.g., grasping a proximal portion of shaft (320), grasping base (312), and/or grasping some other part of uterine manipulator (300)). In such scenarios, uterine manipulator (300) may be coupled with robotic arm (110) after reaching the stage shown in FIG. 6B.

In some other versions, uterine manipulator (300) is already coupled with robotic arm (110) before reaching the stage shown in FIG. 6B; and robotic arm (110) is used to guide and drive uterine manipulator (300) to the position shown in FIG. 6B. As yet another variation, some versions may allow a human operator to guide and drive uterine manipulator (300) to the position shown in FIG. 6B while uterine manipulator (300) is coupled with robotic arm (110), such that robotic arm (110) does not restrict manual movement of uterine manipulator (300) leading up to the stage shown in FIG. 6B.

Regardless of the stage at which uterine manipulator (300) is coupled with robotic arm (110), robotic arm (110) may be positioned in various suitable ways relative to the patient while uterine manipulator (300) is inserted in the patient. In some scenarios, robotic arm (110) crosses over the top of one of the patient's legs from the side, to assist in positioning uterine manipulator (300). In some other scenarios (e.g., when the patient's legs are supported by stirrups), robotic arm (110) crosses under the bottom of one of the patient's legs from the side, to assist in positioning uterine manipulator (300). In still other scenarios, robotic arm (110) is positioned between the patient's legs from underneath, such that robotic arm (110) does not cross over or under either of the patient's legs. Alternatively, robotic arm (110) may have any other suitable spatial and positional relationship with respect to the patient.

In the present example, uterine manipulator (300) is advanced distally until distal end (322) of shaft (320) reaches the fundus (F) of the uterus (U). The operator may determine that distal end (322) has reached the fundus (F) via tactile feedback (e.g., such that the operator can feel sudden resistance to further advancement of shaft (320)). In some cases where distal end (322) contacts the fundus (F), distal end (322) may remain in contact with fundus (F) throughout the rest of the procedure shown in FIGS. 6B-6E. In some other versions, distal end (322) may be slightly backed out proximally, such that distal end (322) does not contact fundus (F) throughout the rest of the procedure shown in FIGS. 6B-6E.

After reaching the state shown in FIG. 6B, balloon (324) may be inflated as described above; and as shown in FIG. 6C. In some cases, balloon (324) is inflated to a point where balloon (324) bears outwardly against the sidewall of the uterus (U). In any case, the inflated balloon (324) may stabilize the distal portion of shaft (320) relative to the uterus (U). Specifically, the inflated balloon (324) may prevent shaft (320) from exiting proximally from the uterus (U) via the cervix (C). Balloon (324) may thus serve as a distally-positioned anchor structure for uterine manipulator (300). The inflated balloon (324) may also provide sufficient engagement between shaft (320) and the uterus (U) to allow use of shaft (320) to reposition and reorient the uterus (U) as described herein.

With balloon (324) in the inflated state the operator may advance sleeve (330) distally along shaft (320) to the position shown in FIG. 6D. In the present example, this is performed by a human operator manually advancing sleeve (330) distally along shaft (320). In some other versions, this may be performed by a robotic operator robotically advancing sleeve (330) distally along shaft (320). As shown, sleeve (330) is advanced distally to a point where distal end (360) is firmly seated in the vaginal fornix (VF). The cervix (C) is received in interior space (354) of body (352). At this stage, the longitudinal position of sleeve (330) along shaft (320) is locked in place via locking ring (340). Specifically, the operator grasps locking ring (340) and rotates locking ring (340) about shaft (320) to firmly lock the position of sleeve (330) along shaft (320). In the present example, this is performed by a human operator, though it may be performed by a robotic operator in other versions. With the position of sleeve (330) locked in place against shaft (320), the position of uterine manipulator (300) is substantially fixed relative to the vagina (V), the cervix (C), and the uterus (U). While balloon (324) serves as a distally-positioned anchor structure for uterine manipulator (300), colpotomy cup (350) serves as a proximally-positioned anchor structure for uterine manipulator (300).

With the position of uterine manipulator (300) being fixed by the combination of balloon (324) and colpotomy cup (350), balloon (332) is inflated as shown in FIG. 6E. Balloon (332) bears outwardly against the sidewall of the vagina (V), thereby creating a fluid-tight seal against the sidewall of the vagina (V).

With uterine manipulator (300) being positioned and configured as shown in FIG. 6E, robotic arm (110) may be utilized to drive uterine manipulator (300) to various positions, to thereby re-orient and reposition the uterus (U) as desired by the clinician who is performing the rest of the medical procedure (e.g., hysterectomy). In some scenarios, the clinician who robotically controls robotic arm (110) to drive uterine manipulator (300) to position and orient the uterus (U) also uses the same robotic system to control instruments that are used to perform a surgical procedure associated with the uterus (U) (e.g., a hysterectomy).

As noted above, by allowing a surgeon to directly control the manipulation of the uterus (U) via robotic arm (110) and uterine manipulator (300), the process avoids potential confusion and inconsistency that might otherwise result in procedures where a human assistant is controlling a uterine manipulator based on commands from another human clinician. Moreover, once the uterus (U) has been manipulated to achieve the desired position and orientation, robotic arm (110) and uterine manipulator (300) may cooperate to maintain this position and orientation of the uterus (U) indefinitely. This may avoid scenarios where a human operator of a uterine manipulator (300) might inadvertently reposition or reorient the uterus (U) in the middle of a medical procedure.

As noted above, one medical procedure that may be performed using robotic arm (110) and uterine manipulator (300) is a hysterectomy. In some versions of such a procedure, one or more cutting instruments are introduced laparoscopically via the patient's abdomen to approach the cervicovaginal junction from outside the uterus (U) and vagina (V). Such instrumentation may be controlled manually or robotically. In versions where the instrumentation is controlled robotically, the same robotic system may control the instrumentation and robotic arm (110). A cutting instrument may cut the uterus (U) away at the cervicovaginal junction, generally tracing around the circular perimeter defined by distal end (360) of colpotomy cup (350).

This cutting at the cervicovaginal junction will ultimately result in separation of the uterus (U) from the vagina (V); and the end of the vagina (V) may be appropriately closed at this point. During this process, the patient's abdomen may be insufflated with pressurized gas, and the pressurized insufflation gas may eventually reach the distal region of the vagina (V). In such scenarios, balloon (332) will provide sealed occlusion that is sufficient to prevent the pressurized insufflation gas from escaping out of the patient via the vagina (V).

While robotic arm (110) and uterine manipulator (300) are described in the foregoing example as being used in a hysterectomy, robotic arm (200) and uterine manipulator (300) may be used in any other suitable fashion and may be used in any other suitable procedures.

Figure 7A:
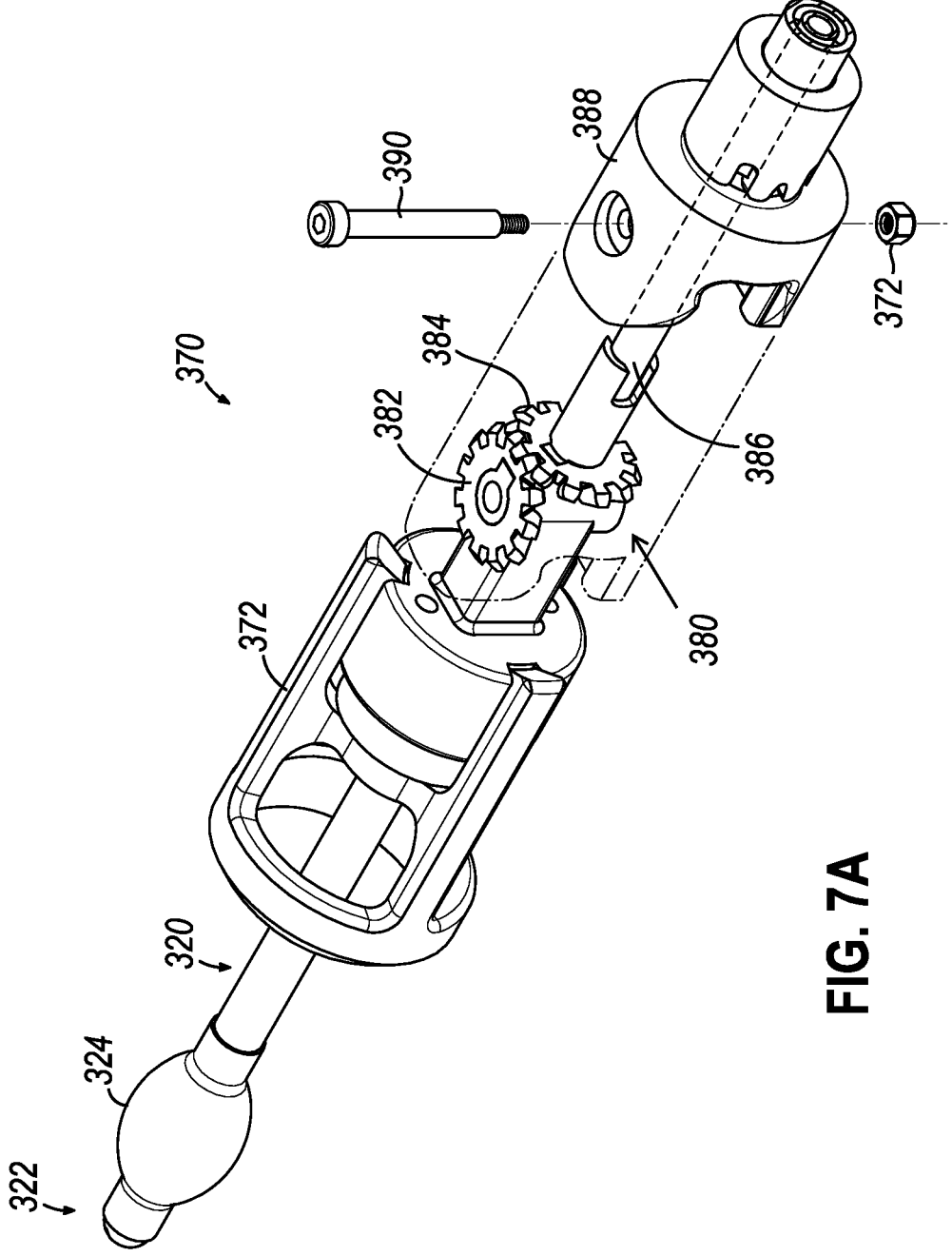
FIG. 7A depicts a partially exploded perspective view of an alternative colpotomy cup.
Figure 7B:
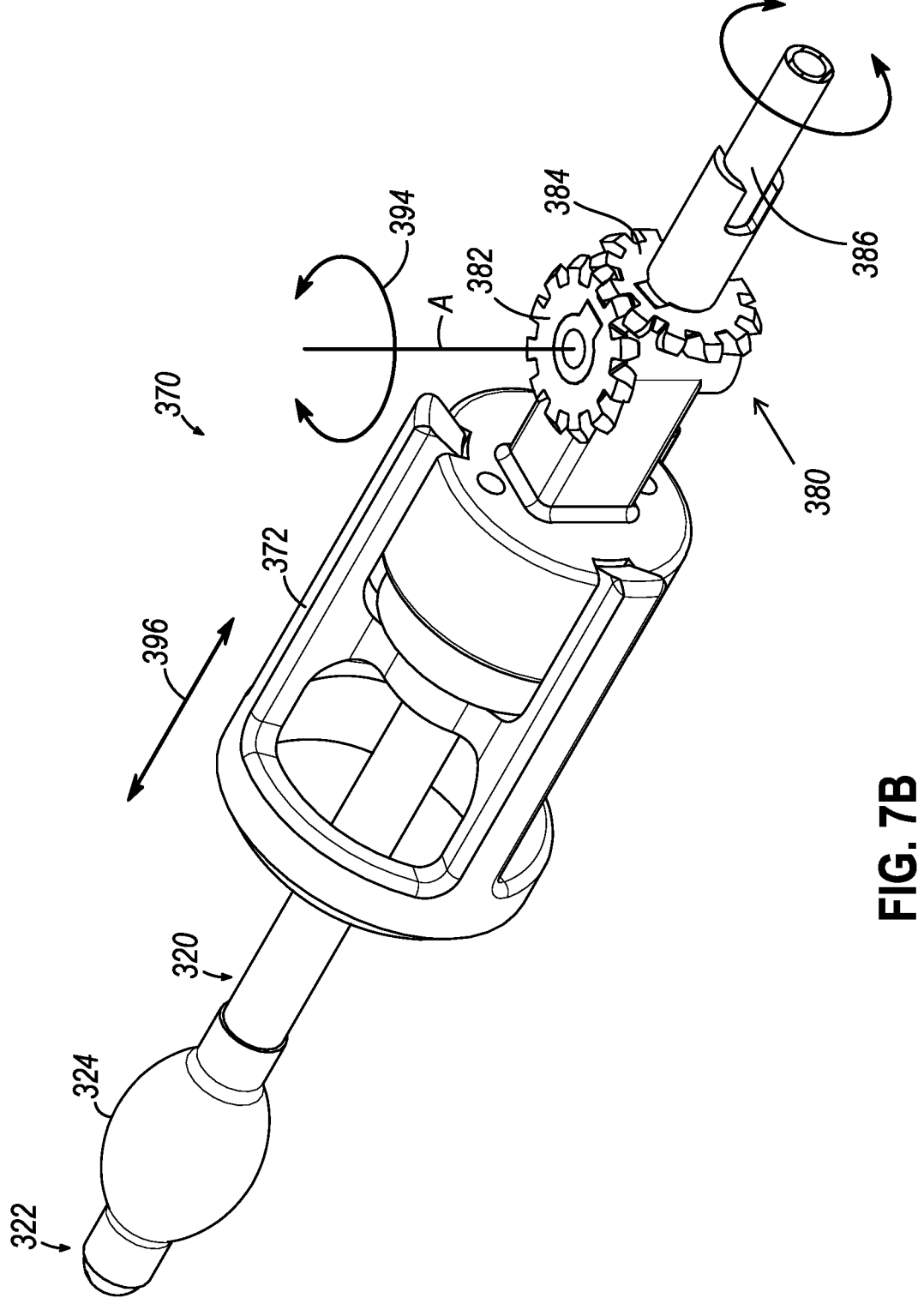
FIG. 7B depicts a perspective view of the colpotomy cup of FIG. 7A.

In some instances, it may be desirable to control the position and orientation of the uterus (U) without moving the proximal portion of uterine manipulator (300) relative to the patient. FIGS. 7A-7B show an alternative colpotomy cup (370) that may be readily incorporated into uterine manipulator (300) described above in replacement of colpotomy cup (350). Therefore, colpotomy cup (370) may translate into a suitable longitudinal position relative to shaft (320), as illustrated by arrow (396) in FIG. 7B, in order to suitably position colpotomy cup (370) relative to shaft (320) in accordance with the description herein.

Colpotomy cup (370) is substantially similar to colpotomy cup (370) described above, with differences elaborated below. In particular, colpotomy cup (370) includes an articulation drive assembly (380) configured to rotate body (372) of colpotomy cup (370) about articulation axis (A), as illustrated by arrow (394), relative to a proximal portion of shaft (320). Shaft (320) extends through colpotomy cup (370) such that rotation of colpotomy cup (370) about articulation axis (A) bends distal end (322) and balloon (324) of shaft (320). Therefore, articulation drive assembly (380) may be utilized to control the position and orientation of the uterus (U) via articulation of colpotomy cup (370) and distal end (322).

In the current example, articulation drive assembly (380) includes a first gear (382), a second gear (384) meshed with the first gear (382), a rotary driver (386) extending proximally within shaft (320) and attached to second gear (384), and a clevis body (388) housing gears (382, 384) via a pin (390) and nut (392). Pin (390) extends through an opening defined by first gear (382), a proximal portion of body (372), and clevis body (388).

Rotary driver (386) extends through clevis body (388) and is configured to rotate relative to clevis body (388) about its own axis. Rotary driver (386) is suitably attached to a rotating input (not shown) located at a proximal end of uterine manipular (300). Rotating input (not shown) is configured to drive rotation of rotary driver (386) about its own longitudinal axis, thereby driving rotation of second gear (384) relative to clevis body (388). Second gear (384) suitably meshes with first gear (382) such that rotation of second gear (384) via rotary driver (386) drives rotation of first gear (382) as indicated by the arrow (394). Therefore, second gear (384) may rotate first gear (382) in a first rotational direction, or an opposite, second, rotational direction. First gear (382) is suitably coupled to body (372) of colpotomy cup (370) such that rotation of first gear (382) drives rotation of body (372) about articulation axis (A) relative to clevis body (388) and the proximal portion of shaft (320), as indicated by arrow (394) shown in FIG. 7B. Therefore, an operator may utilize articulation drive assembly (380) in order to articulate distal end (322) of shaft (320) and colpotomy cup (370) relative to a proximal portion of shaft (320). Such articulation may be utilized when colpotomy cup (370) and shaft (320) are suitably attached to anatomy of a patient in order to position and orient the uterus (U) in accordance with the description herein.

III. Examples of Robotically Controlled Instruments with Patient-Specific Remote Center of Motion Measuring Instruments During use of robotic surgical system (10), while an instrument (24, 114, 300) is inserted into patient and attached to robotic arm (16, 110) in accordance with the description herein, robotic surgical system (10) may define a Remote Center of Motion (RCM) for instrument (24, 114, 300). An RCM is a point in three-dimensional space about which instrument (24, 114, 300) pivots during use. Therefore, as robotic arm (16, 110) actuates instrument (24, 114, 330) in accordance with the description herein, robotic surgical system (10) ensures a portion of instrument (24, 114, 330) always substantially coincides with the RCM throughout all stages of movement of instrument (24, 114, 330). While different portions of instrument (24, 114, 330) may be positioned at the RCM at different stages of movement of instrument (24, 114, 330), some portion of instrument (24, 114, 330) will always be positioned at the RCM during operation of instrument (24, 114, 330).

As mentioned above, tool driver (112) includes a cannula (120) that is configured to promote insertion of instrument (114) into the patient. Cannula (120) is fixed relative to a track of tool driver (112) such that robotic surgical system (10) may determine the location of cannula (120) relative to other components of robotic arm (110) and instrument (114). In some instances, such as during a laparoscopic procedure, cannula (120) may be inserted into the surgically created opening to provide access within the targeted anatomical structure of a patient. In such instances, cannula (120) may remain substantially fixed relative to anatomical structures of a patient. In some cases, cannula (120) includes an RCM marking that is placed at the patient body wall (e.g., abdominal wall); and robotic arm (110) is controlled such that the RCM marking substantially stays at that location throughout the rest of the procedure (even if cannula (120) pivots at the patient body wall). Robotic arm (110) and portions of instrument (24, 114, 330) may also pivot at this region at or near the patient body wall corresponding to the RCM marking on cannula (120). The operable configuration of a robotic arm (110) that constrains the movement of robotic arm (110) to provide consistent positioning of the RCM marked portion of cannula (120) at the patient body wall throughout the procedure may be considered as a hardware RCM. In other words, the robotic arm (110) whose movements are constrained may define and maintain a hardware RCM.

In instances where a patient is supported on platform (14) that extends along a plane that is substantially parallel with the floor, there is little risk of the patient overly shifting or moving along platform (14) during use. However, in instances where hardware (e.g., cannula (120)) is not substantially fixed relative to a patient, and/or there is risk of a patient shifting or moving along platform (14) during example use, it may not be suitable to utilize a hardware RCM or an RCM whose location in three-dimensional space is otherwise fixed throughout a procedure. As one example, when instrument (24, 114, 300) is being used to access a naturally occurring orifice (such as when uterine manipulator (300) is inserted through the vagina (V) into the uterus (U) via the cervix (C)), the position of the patient may not remain substantially fixed throughout the procedure, such that a dynamic RCM may be more dynamic than a purely static RCM. Further, targeted anatomical structures in relation to the naturally occurring orifice may deviate from patient to patient. In instances where uterine manipulator (300) is being used, the distance between the vaginal entry point, the cervix (C), and the fundus (F) of the uterus (U) may deviate from patient to patient, such that the desired RCM needs to be calculated for each specific patient, rather than utilizing a hardware RCM described above. Therefore, it may be desirable to provide a suitable means of determining the RCM for instrument (24, 114, 300) where the RCM is defined, at least in part, by the anatomy of the patient at hand.

Similarly, it may be desirable to allow the position of the RCM to change during a procedure, particularly in cases where the patient is supported on platform (14) along a plane that is not parallel with the floor. For example, when uterine manipulator (300) is utilized, a patient may be elevated at an angle on platform (14) (e.g., in the Trendelenburg position). In such instances, the patient may be at risk of sliding down platform (14) due to gravity and/or other forces, which may also change the RCM relative to hardware, and/or require adjustments of the patient and/or surgical equipment, prior to resuming a surgical procedure. Therefore, it may be desirable to provide a suitable means for determining if the patient has shifted along platform (14) during a surgical procedure; to thereby provide dynamic adjustment of the RCM.

Figure 8:
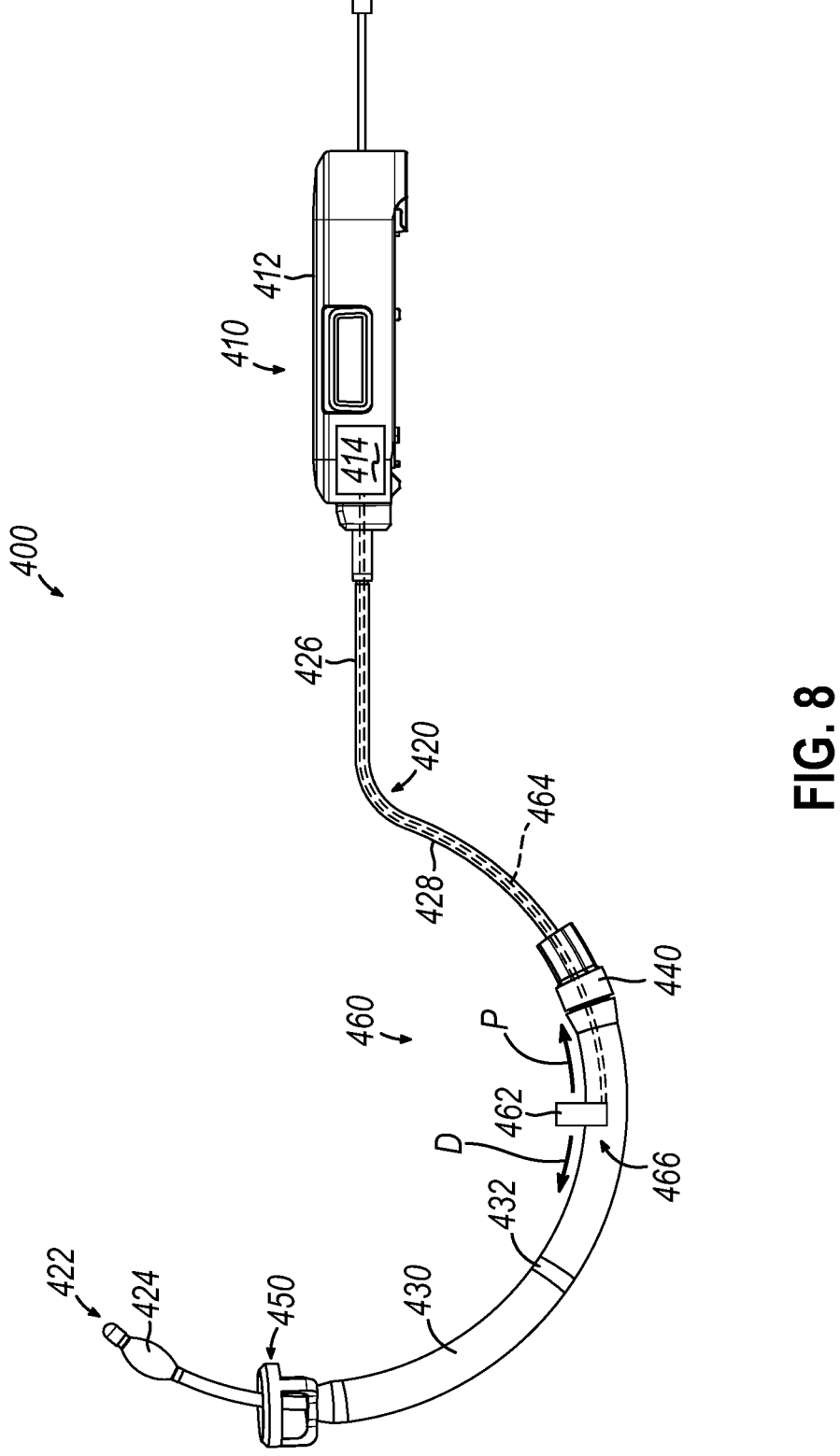
FIG. 8 depicts an elevational side view of another example of a uterine manipulator.
Figure 9A:
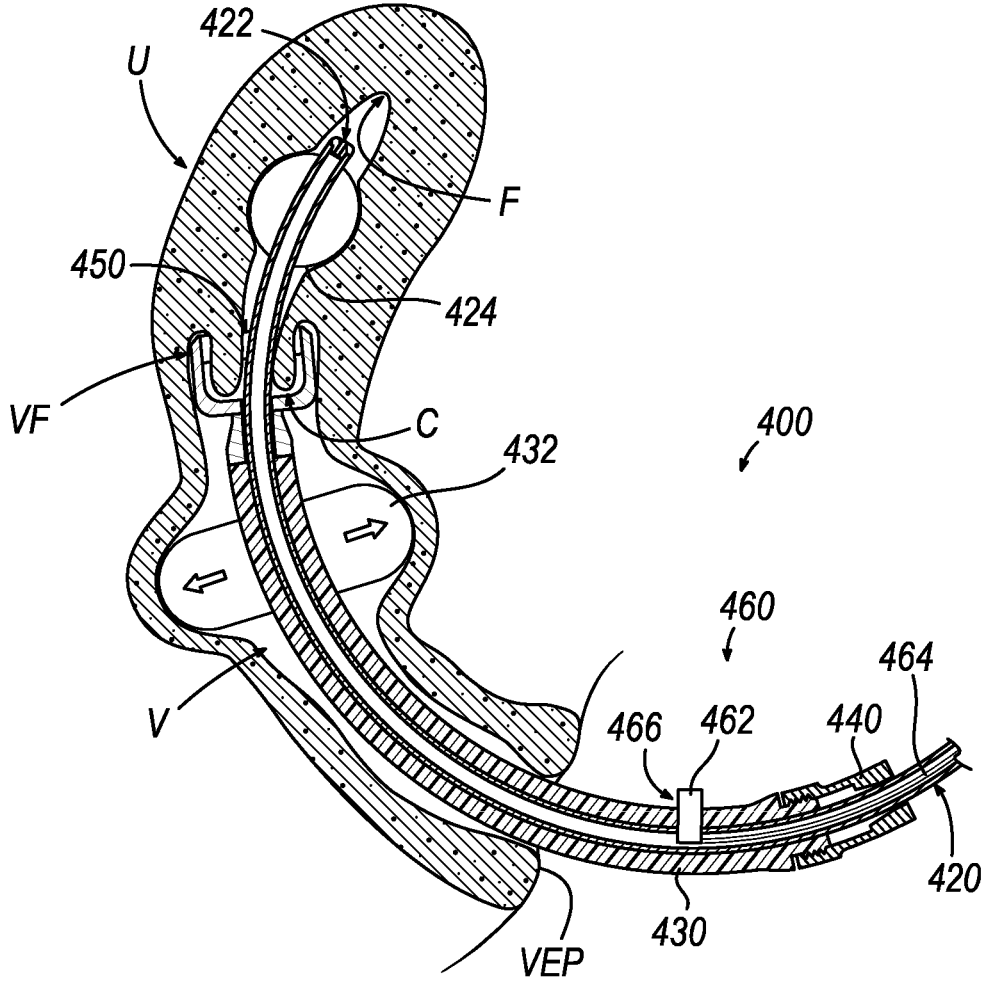
FIG. 9A depicts a mid-sagittal cross-sectional view of the vagina and uterus of FIG. 6A, with the uterine manipulator of FIG. 8 operatively engaged with the vagina and uterus, with a Remote Center of Motion (RCM) measuring instrument of the uterine manipulator in a proximal, disengaged, position.
Figure 9B:
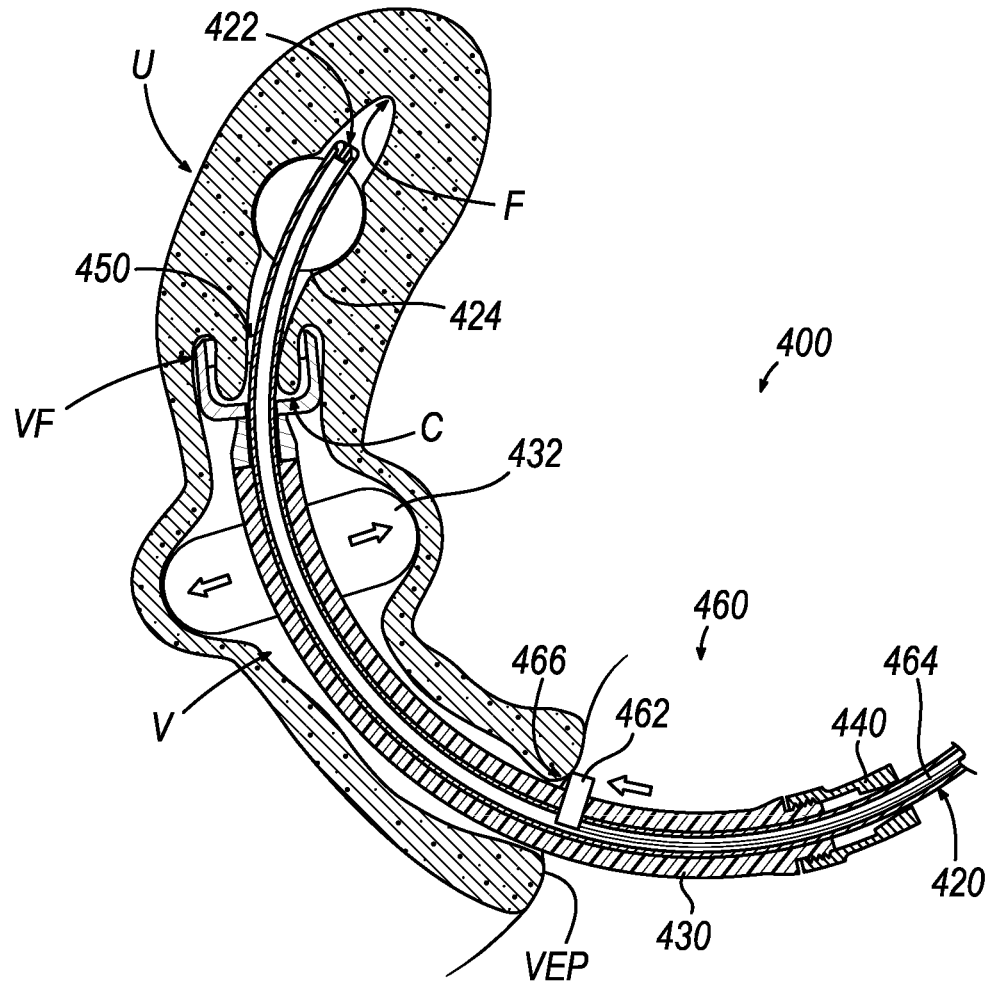
FIG. 9B depicts a mid-sagittal cross-sectional view of the vagina and uterus of FIG. 6A, with the uterine manipulator of FIG. 8 operatively engaged with the vagina and uterus, with the RCM measuring instrument of FIG. 9B actuated into a distal, engaged, position.

FIGS. 8-9B show an example of a robotic instrument, in the form of a uterine manipulator (400), that is configured to measure a patient-specific RCM in conjunction with robotic surgical system (10). Uterine manipulator (400) may be substantially similar to uterine manipulator (300) described above, with differences elaborated below. Uterine manipular (400) thus includes a tool driver interface (410), base (412), a shaft (420), a distal end (422), a balloon (424), a linear portion (426), a curved portion (428), a sleeve (430), a balloon (432), a locking ring (440), and a colpotomy cup (450); which may be substantially similar to tool driver interface (310), base (312), distal end (322), balloon (324), linear portion (426), curved portion (328), sleeve (330), balloon (332), locking ring (340), and colpotomy cup (350) described above, with differences elaborated below.

Uterine manipulator (400) also includes an RCM measuring instrument (460). As will be described in greater detail below, RCM measuring instrument (460) is configured to measure the distance between an anatomical structure (e.g., a naturally occurring orifice such as the vaginal entry point (VEP)) and a known position of uterine manipulator (400) and/or robotic arm (116). Robotic surgical system (10) may then utilize the measured distance between the anatomical structure and the known position of manipulator (400) and/or robotic arm (116) in order to calculate an RCM at or near the anatomical structure (e.g., the naturally occurring orifice such as the vaginal entry point (VEP) shown in FIGS. 9A-9B). Robotic surgical system (10) may restrict the movement of robotic arm (110) and uterine manipulator (400) such that uterine manipulator (400) pivots about the newly calculated RCM; and such that a portion of uterine manipulator (400) remains positioned at RCM throughout operation of uterine manipulator (400).

RCM measuring instrument (460) in the current example includes a rotating tool drive input (414) associated with tool driver interface (410), a contact paddle (462) slidably disposed along a guide track (466) of sleeve (430), and an elongated actuating body (464) slidably disposed within shaft (420) between rotating tool drive input (414) and contact paddle (462). Rotating tool drive input (414) is configured to couple with a motor (not shown) of tool driver (112) such that the motor (not shown) of tool driver (112) may drive rotation of rotating tool drive input (414) in a first angular direction, and a second, opposite, angular direction. Therefore, an operator at control console (28) may instruct a motor (not shown) of tool driver (112) to drive rotation of rotating tool drive input (414). Additionally, suitable components of robotic surgical system (10) may track the angular displacement of rotating tool drive input (414) and/or the motor (not shown) of tool driver (112) operatively coupled to rotating tool drive input (414). As will be described in greater detail below, the angular displacement of rotating tool drive input (414) is indicative of the location of contact paddle (462) along curved portion (428) of shaft (422).

Contact paddle (462) is slidably disposed relative to shaft (420) and sleeve (430) of uterine manipulator (400). In particular, shaft (420) and sleeve (430) cooperatively define a guide track (466) that slidably houses contact paddle (462), thereby allowing contact paddle (462) to slide both proximal and distally, as indicated by the movement arrows (P. D) in FIG. 8, respectively.

With contact paddle (462) being slidably disposed within sleeve (430), sleeve (430) may be actuated distally relative to contact paddle (462) in order allow colpotomy cup (450) to serve as the proximally-positioned anchor structure for uterine manipulator (400) in accordance with the description herein. As will be described in greater detail below, once and/or prior to uterine manipulator (400) being suitably anchored to the uterus (U), contact paddle may be actuated, in accordance with the description herein, into engagement with vaginal entry point (VEP).

Elongate actuating body (464) is slidably disposed within shaft (420). Further, elongate actuating body (464) is fixed at its distal end to contact paddle (462). Therefore, movement of elongate actuating body (464) within shaft (420) drives corresponding movement of contact paddle (462) relative to shaft (420). A proximal end of elongate actuating body (464) is suitably coupled to rotating tool drive input (414) such that rotation of tool drive input (414) in a first angular direction drives the distal end of elongate actuating body (464) distally, and such that rotation of tool drive input (414) in a second, opposite, angular direction drives the distal end of elongate actuating body (464) proximally. Elongate actuating body (464) and tool drive input (414) may include any suitable structure to achieve such results as would be apparent to one skilled in the art in view of the teachings herein. For example, elongate actuating body (464) may include a wire while tool drive input (414) may include a suitable spool configured to both feed and wind-up the wire. Such a wire would have sufficient rigidity in order to drive contact paddle (462) distally but have sufficient flexibility in order to be wound up and fed from spool.

As mentioned above, tool driver (112) may rotate tool drive input (414) while suitable components of robotic system (10) may track the angular displacement of tool drive input (414). Since rotation of tool drive input (414) predictably actuates the distal end of elongate actuating body (464) and contact paddle (462) relative to shaft (420), robotic system (10) may utilize the angular displacement to tool drive input (414) to calculate the location of contact paddle relative to shaft (420). In instances where at least the proximal portion of shaft (420) is substantially rigid enough such that the position of the proximal portion of shaft (420) is known relative to tool driver interface (410), robotic system (10) may utilize the known geometry to calculate to spatial positioning of contact paddle (462) relative to tool driver (112), thereby determining the spatial positioning of contact paddle (462) relative to robotic arm (110). As will be described in greater detail below, the spatial position of contact paddle (462) is utilized to calculate the RCM for uterine manipulator (400) and the anatomical dimensions of a specific patient.

FIGS. 9A-9B show an illustrative use of RCM measuring instrument (460) being utilized in order to assist a robotic surgical system (10) in determining the RCM for uterine manipulator (400) controlled by robotic arm (110). First, as shown in FIG. 9A, uterine manipulator (400) is suitably anchored to the uterus (U) in accordance with the description herein. Additionally, as shown in FIG. 9A, contact paddle (462) is positioned proximally relative to vaginal entry point (VEP). In the current example, vaginal entry point (VEP) is the desired RCM for uterine manipulator (400). Next, as shown in FIG. 9A, the operator may advance contact paddle (462) in accordance with the description herein until contact paddle (462) suitably engages suitable anatomical structure adjacent to vaginal entry point (VEP). Suitable engagement may be determined via visual confirmation or any other suitable means as would be apparent to one skilled in the art in view of the teachings herein. For example, contact paddle (462) may have an engagement sensor configured to determine when a surface of contact paddle (462) suitably contacts an anatomical structure.

Once contact paddle (462) is determined to be in suitable engagement, robotic system (10) may determine the position of contact paddle (462) relative to other components of robotic arm (110) and/or manipulator (400). Robotic system (10) may then further utilize the position of contact paddle (462) in order to determine the RCM for manipulator (400), as well as robotic arm (110) controlling manipulator (400).

Figure 10A:
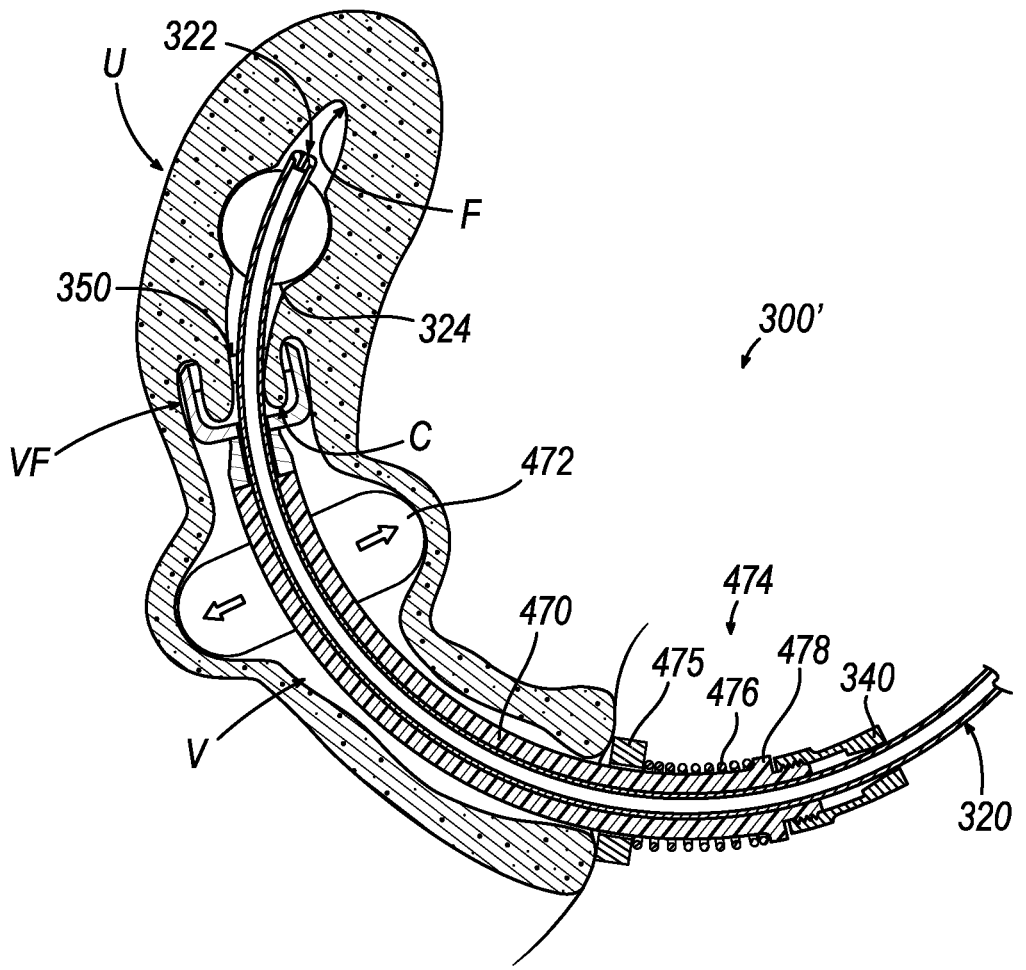
FIG. 10A depicts a mid-sagittal cross-sectional view of the vagina and uterus of FIG. 6A, with a uterine manipulator operatively engaged with the vagina and uterus.
Figure 10B:
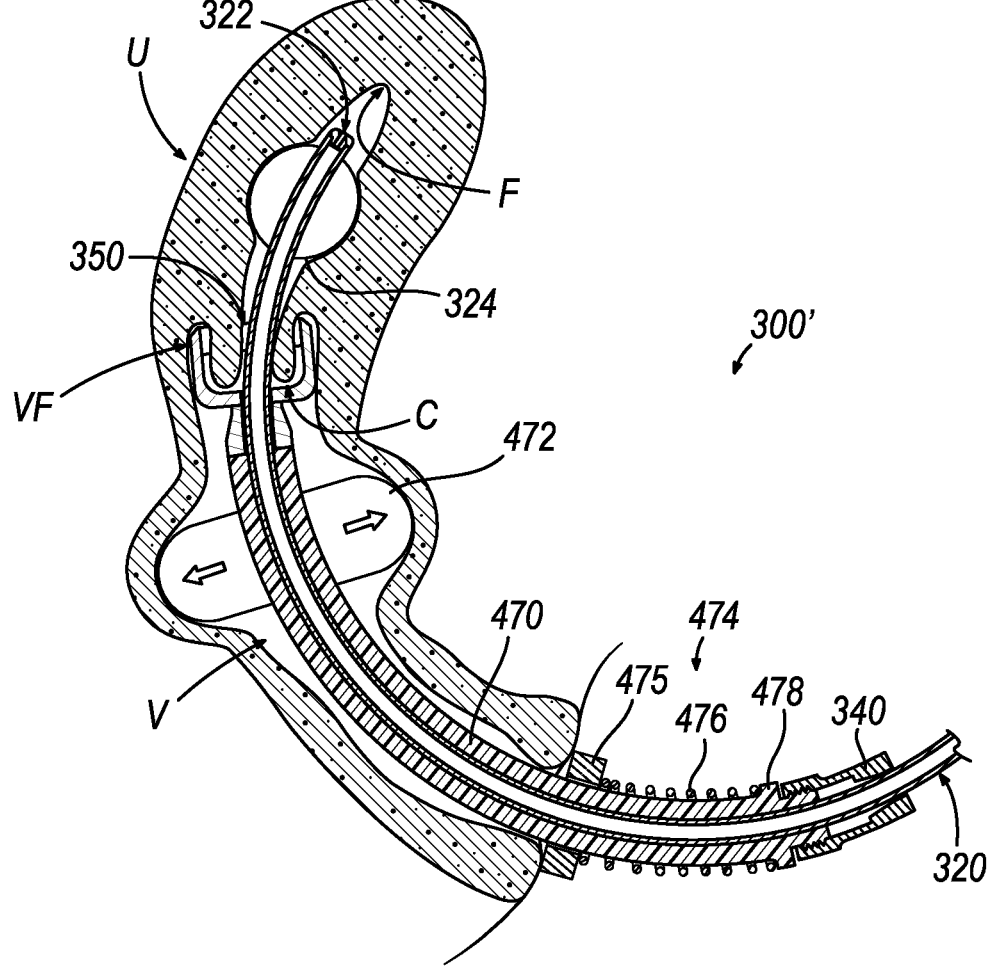
FIG. 10B depicts a mid-sagittal cross-sectional view of the vagina and uterus of FIG. 10A, where the uterus has migrated from the position shown in FIG. 10A.

In some instances, the anchoring features of uterine manipulator (300, 400) may decouple from anatomical structures of a patient. For example, colpotomy cup (350, 450) may undesirably migrate off the cervix (C). Additionally, as mentioned above, in some instances, a patient may undesirably move on platform (14). Therefore, it may be desirable to visually confirm if a patient has been unintentionally repositioned relative to uterine manipulator (300, 400) after anchoring of such a uterine manipulator in accordance with the description herein. FIGS. 10A-10B show an alternative uterine manipulator (300') that may be substantially similar to uterine manipulator (300, 400) described above, but with an alternative sleeve (470) being incorporated in replacement of sleeve (330, 430). Sleeve (470) is substantially similar to sleeve (330, 430) described above, with differences described herein. Sleeve (470) thus includes a balloon (472) that is substantially similar to balloon (332, 432) described above.

Sleeve (470) also includes a visual migration indicator (474) configured to visually display if a patient has undesirably moved relative to sleeve (470) after uterine manipulator (300') has been anchored in accordance with the description herein. Visual migration indicator (474) includes an engagement tab (475), a spring (476), and a proximal grounding collar (478). Spring (476) is interposed between engagement tab (475) and collar (478). Spring (476) imparts a distal bias on engagement tab (475) such that as sleeve (470) is actuating in order to anchor colpotomy cup (350) with the cervix (C) in accordance with the description herein, spring (476) compresses due to engagement tab (475) contacting the vaginal entry point (VEP).

In cases where the patient is in the Trendelenburg position, if the patient slides downwardly on platform (14) or otherwise shifts away from uterine manipulator (300'), support spring (476) may expand, as shown in FIG. 10B, thereby driving engagement tab (475) distally along sleeve (470). In some other scenarios, the patient may shift position on platform (14) such that the patient moves toward uterine manipulator (300'), thereby compressing support spring (476) and driving engagement tab (475) proximally along sleeve (470). In either case, the movement of engagement tab (475) would visually convey to an operator that uterine manipulator (300') is no longer suitably positioned. Conversely, if colpotomy cup (350) is no longer anchoring the cervix (C), the cervix (C) may move distally relative to colpotomy cup (350). Such distal movement of the cervix (C) may lead to engagement tab (475) also being advanced distally relative to sleeve (470). Such movement of engagement tab (475) would visually convey to an operator that uterine manipulator (300') is no longer suitably positioned.

Figure 11:
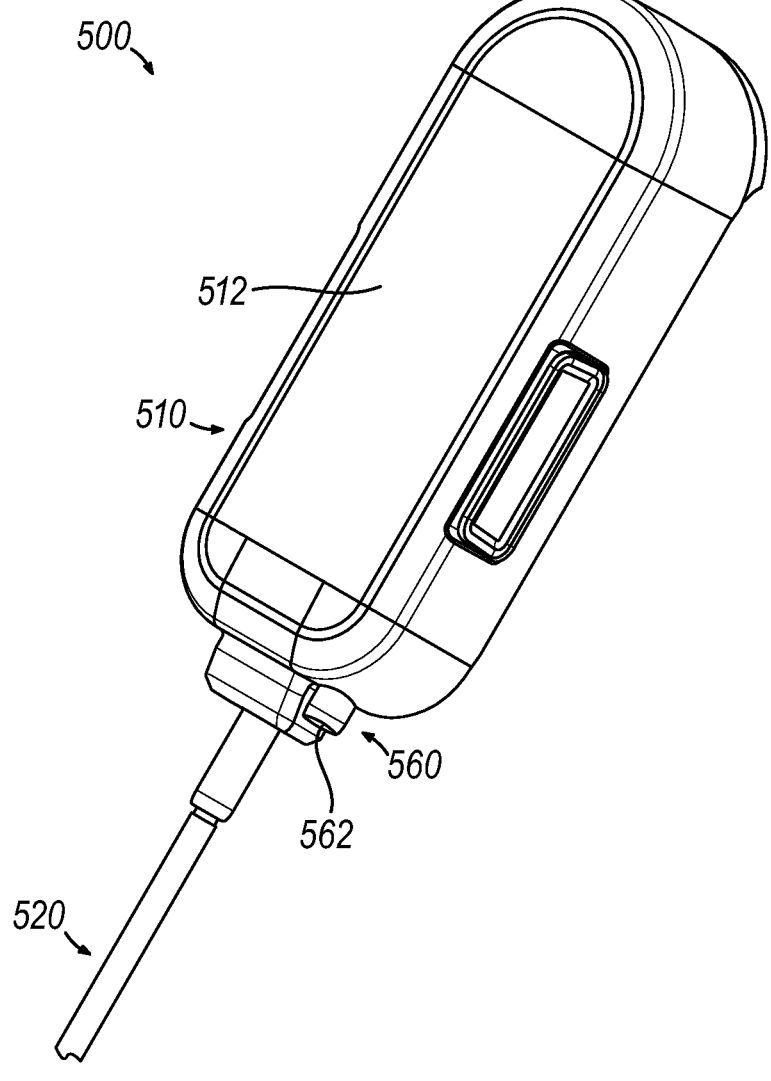
FIG. 11 depicts a perspective view of a tool driver interface.
Figure 12:
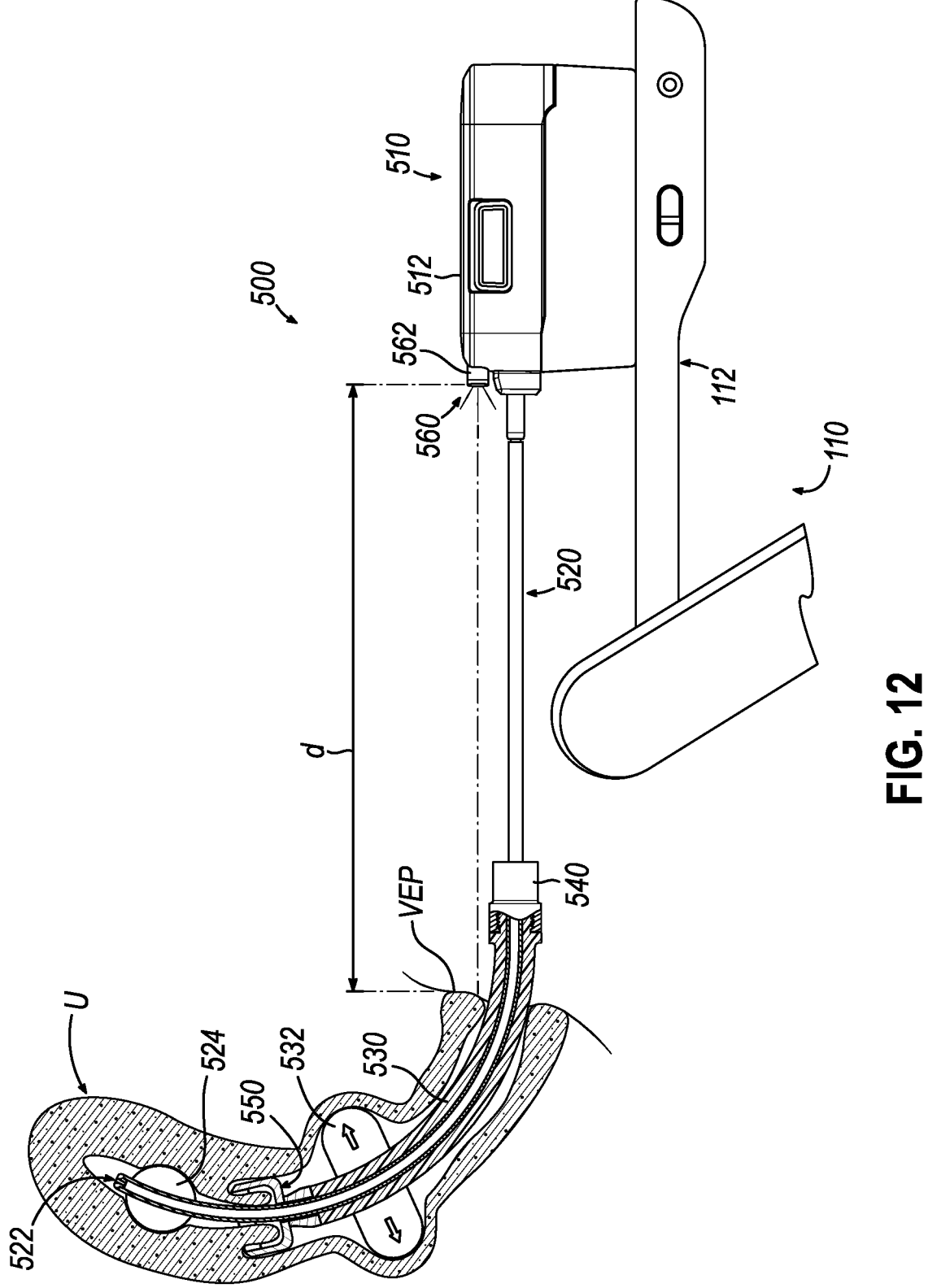
FIG. 12 depicts a mid-sagittal cross-sectional view of the vagina and uterus of FIG. 6A with a uterine manipulator operatively engaged with the vagina and uterus.

FIGS. 11-12 show another example of a robotic instrument, in the form of a uterine manipulator (500), that is configured to measure a patient-specific RCM in conjunction with robotic surgical system (10). Uterine manipulator (500) may be substantially similar to uterine manipulator (300, 300', 400) described above, with differences elaborated below. Uterine manipular (500) thus includes a tool driver interface (510), a base (512), a shaft (520), a distal end (522), a balloon (524), a sleeve (530), a balloon (532), a locking ring (540), and a colpotomy cup (550); which may be substantially similar to tool driver interface (310), base (312), shaft (320), distal end (322), balloon (324), sleeve (330), balloon (332), locking ring (340), and colpotomy cup (350) described above, with differences elaborated below.

Uterine manipulator (500) also includes an RCM measuring instrument (560). In the current example, RCM measuring instrument (560) include an optical sensor (562) fixedly attached to base (512) of tool driver interface (510). Optical sensor (562) is configured to optically measure the distance (d) between an anatomical structure (e.g., a naturally occurring orifice such as the vaginal entry point (VEP)) and a known position of uterine manipulator (500) and/or robotic arm (110). Optical sensor (562) may communicate data associated with the optically measured distance to suitable component of robotic surgical system (10). As shown in FIG. 12, optical sensor (562) is distally facing and configured to be aligned with the vaginal entry point (VEP) once uterine manipulator (500) is suitably anchored to the uterus (U) in accordance with the description herein.

Robotic surgical system (10) may then utilize the measured distance between the anatomical structure and the known position of manipulator (500) and/or robotic arm (110) in order to calculate the RCM at or near the anatomical structure (e.g., the naturally occurring orifice such as the vaginal entry point (VEP) shown in FIG. 12). Robotic surgical system (10) may restrict the movement of robotic arm (110) and uterine manipulator (500) such that uterine manipulator (500) pivots about the newly calculated RCM; and such that a portion of uterine manipulator (500) remains positioned at RCM throughout operation of uterine manipulator (500).

Figure 13:
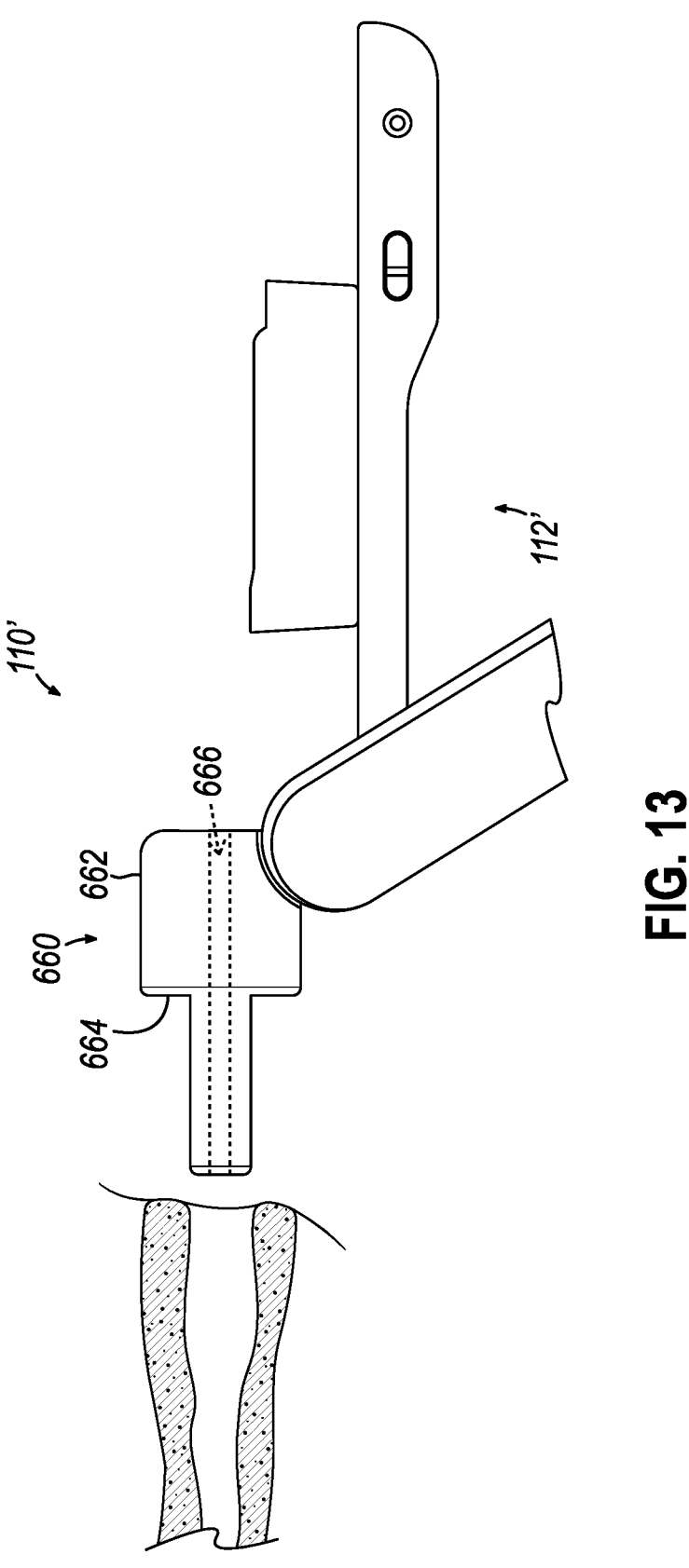
FIG. 13 depicts an elevational side view of a tool driver with a cannula having an RCM measuring instrument.

FIG. 13 shows an alternative robotic arm (110') that may be used in replacement of robotic arm (110) described above. Robotic arm (110) is substantially similar to robotic arm (110) described above, with differences elaborated below. In particular, robotic arm (110') includes an alternative tool driver (112') that has an RCM measuring cannula (660). RCM measuring cannula (660) includes a cannula body (662) defining a channel (666), and a force-sensing distally-presented (FSDP) surface (664). Cannula (660) is fixed to the rest of alternative tool driver (112') such that the location of FSDP surface (664) is known by a robotic surgical system (10) utilizing robotic arm (110'). FSDP surface (664) includes a sensor (e.g., strain gauge, etc.) that is configured to detect and measure when a force is acting on FSDP surface (664). FSDP surface (664) is in communication with suitable components of robotic system (10) such that robotic system (10) may receive data obtained from FSDP surface (664). FSDP surface (664) may be actuated into engagement with a naturally occurring orifice (e.g., a vaginal entry point (VEP)). Since the location of FSDP surface (664) is known by robotic system (10), robotic system (10) may utilized the data obtained from FSDP surface (664) once engaged with the naturally occurring orifice in order to determine the RCM of an instrument coupled to robotic arm (110').

Figure 14:
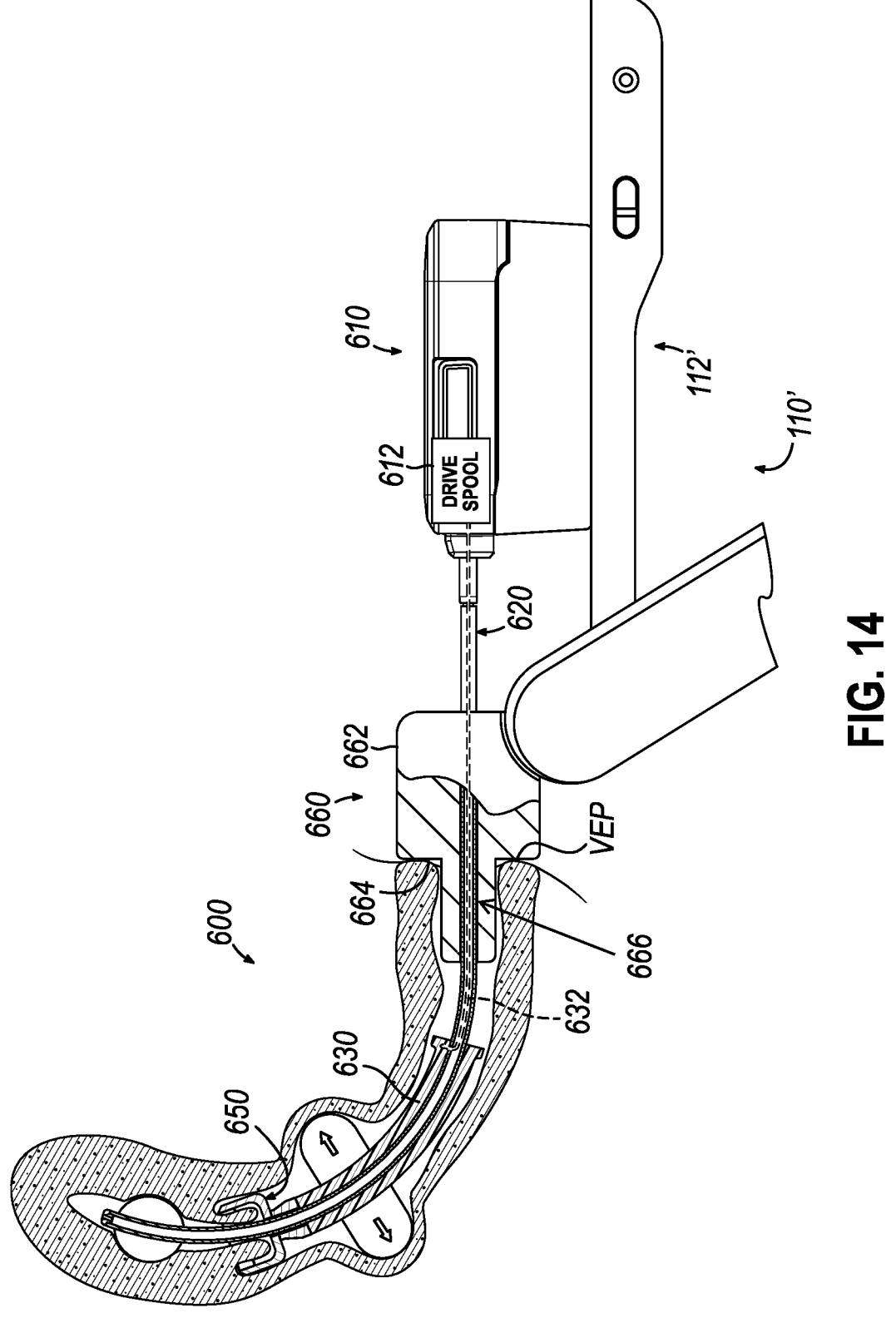
FIG. 14 depicts a mid-sagittal cross-sectional view of the vagina and uterus of FIG. 6A with a uterine manipulator operatively engaged with the vagina and uterus while being attached to the tool driver of FIG. 13.

Robotic arm (110') may be used in conjunction with uterine manipulator (600) shown in FIG. 14. Uterine manipulator (600) may be substantially similar to uterine manipulator (300, 300', 400, 500) described above, with differences elaborated below. Uterine manipular (600) thus includes a tool driver interface (610), a shaft (620), a sleeve (630), a colpotomy cup (650); which may be substantially similar to tool driver interface (310), sleeve (330), locking ring (340), and colpotomy cup (350) described above, with differences elaborated below.

Shaft (620) extends through channel (666) defined by cannula body (662). In some instances, shaft (620) is slidably housed within channel (666). Sleeve (630) is coupled to an elongated actuating body (632) that is slidably disposed within shaft (620). Elongated actuating body (632) is coupled to a drive spool (612) housed within tool driver interface (610). Drive spool (612) is coupled to a motor (not shown) in tool driver (112) such that the motor may rotate drive spool (612). Rotation of drive spool (612) may actuate elongated actuating body (632) and sleeve (630) such that sleeve (630) may be translated along shaft (620) via the motor, drive spool (612), and elongated actuating body (632). Therefore, shaft (620) may be suitably positioned within the uterus (U) via movement of tool driver interface (610); while sleeve (630) may be suitably positioned via drive spool (612) and elongated actuating body (632).

As mentioned above, FSDP surface (664) is configured to detect and measure when a force is acting on FSDP surface (664). Therefore, robotic arm (110') may be actuated until FSDP surface (664) is in contact with vaginal entry point (VEP). FSDP surface (664) may communicate such contact with suitable components of robotic system (10), which also knows the spatial position of FSDP surface (664) at the same time.

Robotic surgical system (10) may then utilize the information obtained from FSDP surface (664), and the known position of FSDP surface (664), in order to calculate an RCM at or near the anatomical structure (e.g., the naturally occurring orifice such as the vaginal entry point (VEP) shown in FIG. 14). Robotic surgical system (10) may restrict the movement of robotic arm (110') and uterine manipulator (600) such that uterine manipulator (600) pivots about the newly calculated RCM; and such that a portion of uterine manipulator (600) remains positioned at RCM throughout operation of uterine manipulator (600).

Additionally, FSDP surface (664) may communicate a force value to robotic surgical system (10). If such a force value exceeds a predetermined threshold, this may be indicative of a patient moving proximally toward cannula body (662). Robotic surgical system (10) may then indicate to an operator or others that the patient has moved relative to robotic arm (110) and uterine manipulator (600) such that the patient or instrumentation should be adjusted. Conversely, if FSDP surface (664) disengages from the vaginal entry point (VEP), this may indicate the RCM is no longer accurate. Robotic surgical system (10) may then indicate to an operator or other that an adjustment needs to be made.

Figure 15A:
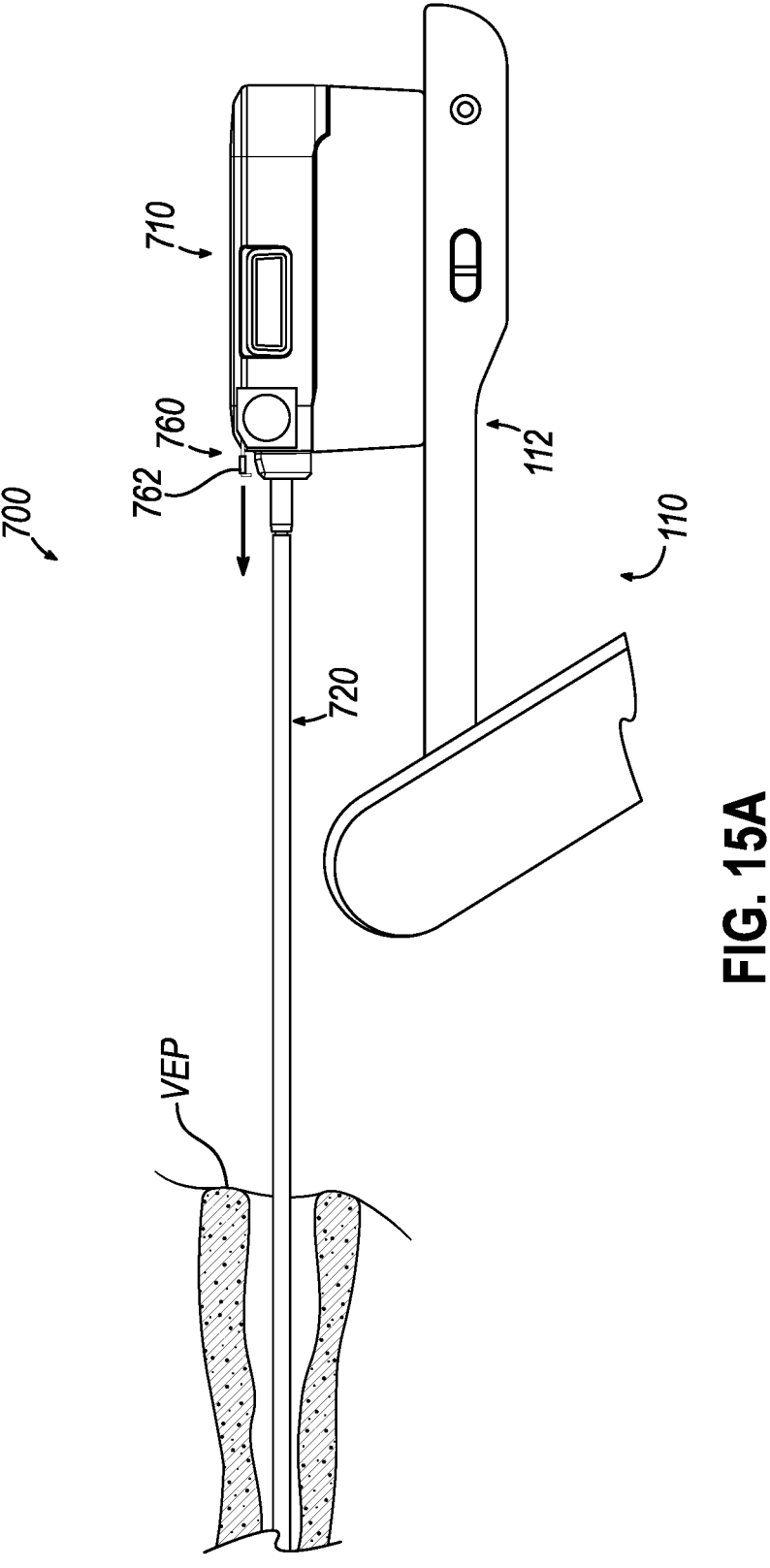
FIG. 15A depicts an elevational side view of an alternative uterine manipulator with an RCM measuring instrument in a retracted position.
Figure 15B:
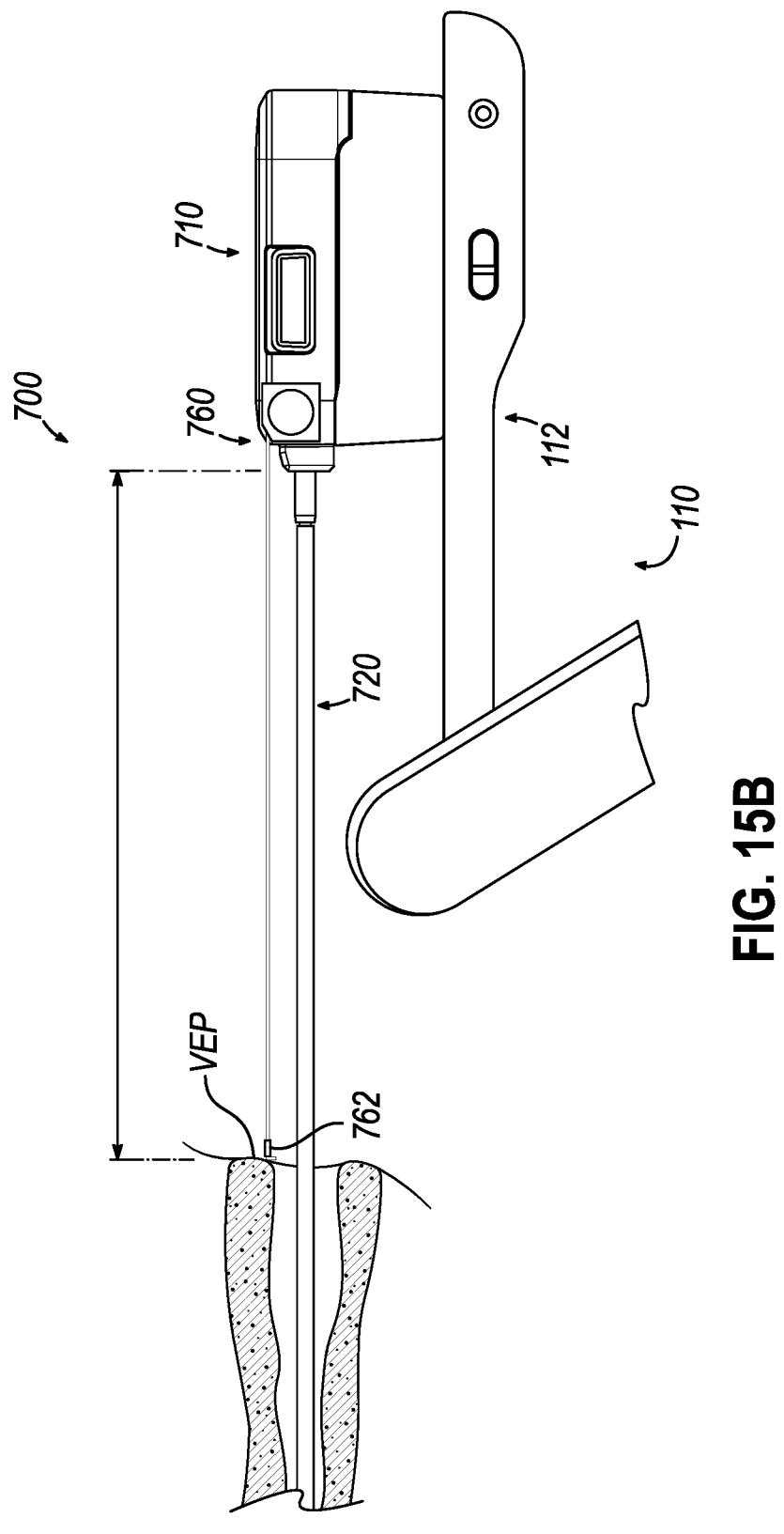
FIG. 15B depicts an elevational side view of the uterine manipulator of FIG. 15A, with the RCM measuring instrument in an extended position.

FIGS. 15A-15B show an example of a robotic instrument, in the form of a uterine manipulator (700), that is configured to measure a patient-specific RCM in conjunction with robotic surgical system (10). Uterine manipulator (700) may be substantially similar to uterine manipulator (300, 300', 400, 500, 600) described above, with differences elaborated below. Uterine manipular (700) thus includes a tool driver interface (710) and a shaft (720); which may be substantially similar to tool driver interface (310) and shaft (320) described above, with differences elaborated below.

Uterine manipulator (700) also includes an RCM measuring instrument (760). In the current example, RCM measuring instrument (760) includes an extendable and retractable distance measurer (762) attached to tool driver interface (710). Extendable and retractable distance measurer (762) is configured and operable similar to a tape measure in this example. Extendable and retractable distance measurer (762) is configured to measure the distance between an anatomical structure (e.g., a naturally occurring orifice such as the vaginal entry point (VEP)) and a known position tool driver interface (710) once uterine manipulator (700) is suitably anchored in accordance with the description herein. In some instances, a user may read the distance on extendable and retractable distance measurer (762) once suitably engaged with the desired anatomical structure; and enter that information manually into robotic system (10). In some instances, extendable and retractable distance measurer (762) may automatically communicate data associated with the measured distance to suitable component of robotic surgical system (10). For instance, extendable and retractable distance measurer (762) may include a sensor that generates a signal indicating the length of extension of extendable and retractable distance measurer (762) once extendable and retractable distance measurer (762) has been brought into engagement with the anatomical structure. Extendable and retractable distance measurer (762) may be biased into the retracted configuration as shown in FIG. 15A.

Robotic surgical system (10) may then utilize the measured distance between the anatomical structure and the known position of manipulator (700) in order to calculate an RCM at or near the anatomical structure (e.g., the naturally occurring orifice such as the vaginal entry point (VEP) shown in FIGS. 15A-15B). Robotic surgical system (10) may restrict the movement of robotic arm (110) and uterine manipulator (700) such that uterine manipulator (700) pivots about the newly calculated RCM; and such that a portion of uterine manipulator (700) remains positioned at RCM throughout operation of uterine manipulator (700).

IV. Illustrative Uterine Manipulator Dual Drive Points from Robotic Arm

Figure 16:
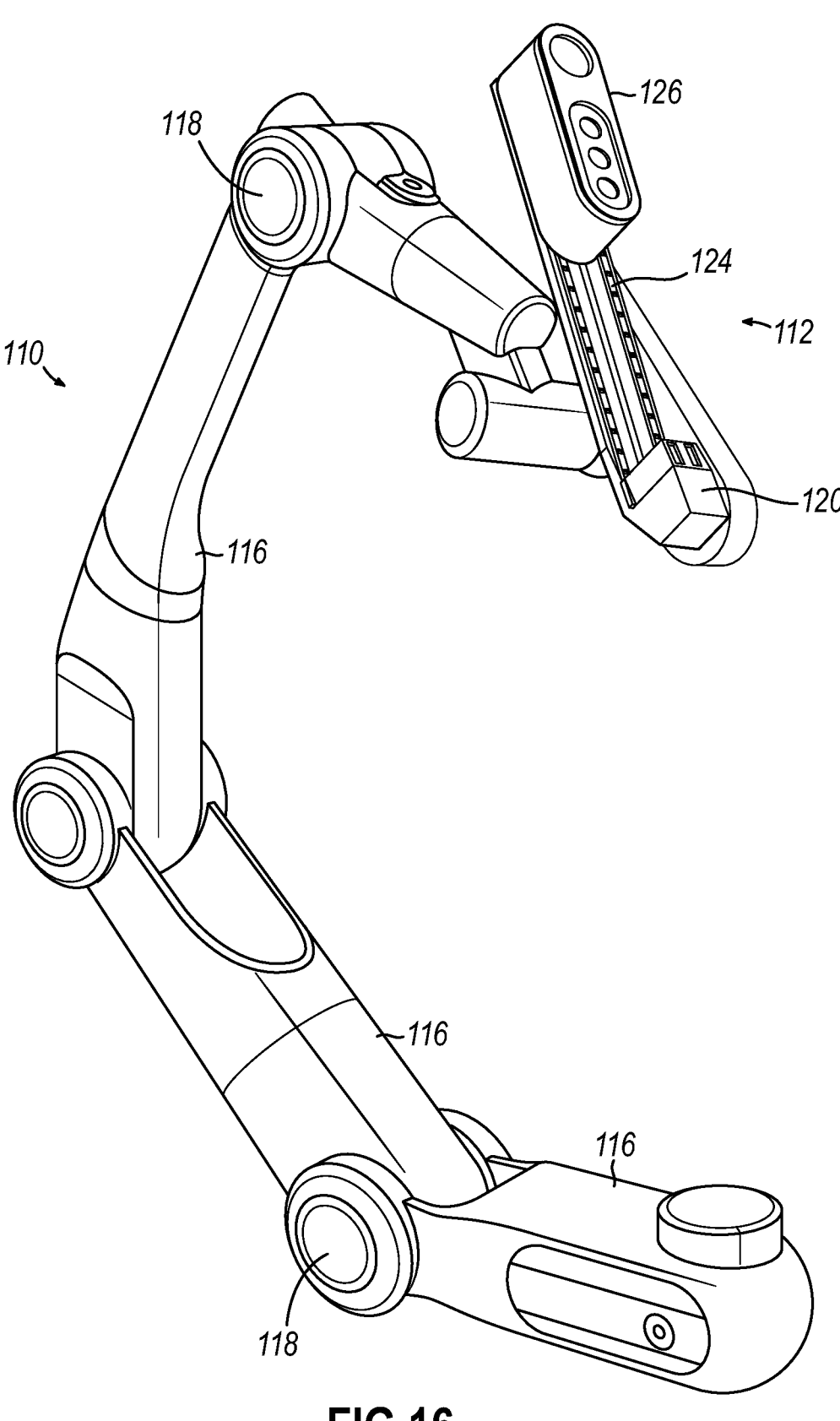
FIG. 16 depicts a perspective view of the robotic arm of FIG. 2.

In instances when the RCM is known, and uterine manipulator (300, 400, 500, 600, 700) is being advanced and/or retracted during use via movement of the robotic arms; it may be desirable to move uterine manipulator (300, 400, 500, 600, 700) along an arcuate path to prevent undue patient trauma. Turning to FIG. 16, movement of uterine manipulator (300, 400, 500, 600, 700) may be accomplished by mounting shaft (320, 430, 530, 620, 720) to cannula mount (120) while keeping a carriage (126) affixed on a stage (124). Alternatively, movement of uterine manipulator (300, 400, 500, 600, 700) may be accomplished by slidably mounting shaft (320, 430, 530, 620, 720) to cannula mount (120) while allowing carriage (126) to translate on stage (124) to further drive translation of uterine manipulator (300, 400, 500, 600, 700). In either circumstance, links (116) and joints (118) may be utilized to cooperatively actuate uterine manipulator (300, 400, 500, 600, 700) in accordance with the description herein.

Figure 17A:
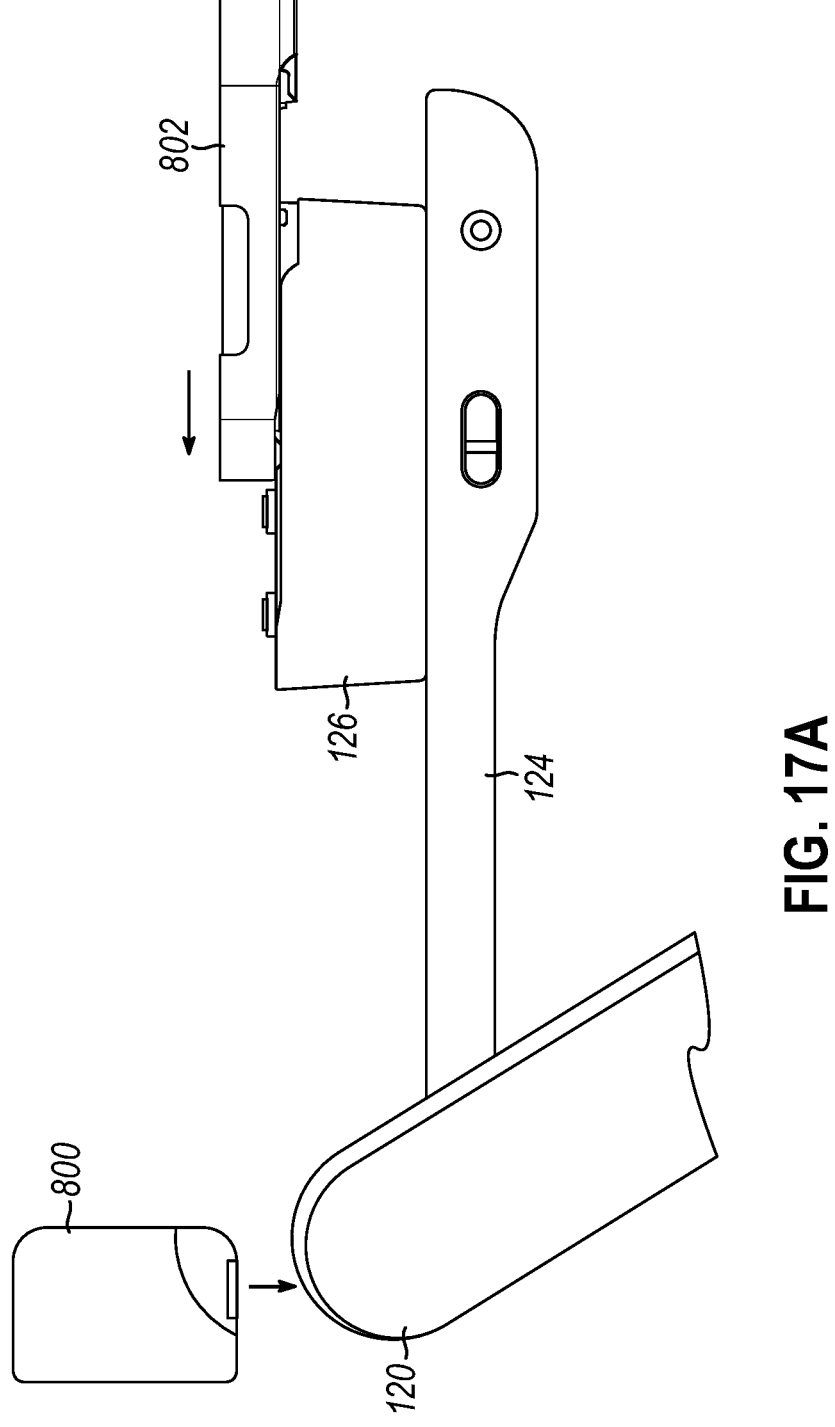
FIG. 17A depicts an elevational side view of a pair of adapter bodies being initially coupled to the robotic arm of FIG. 2.
Figure 17B:
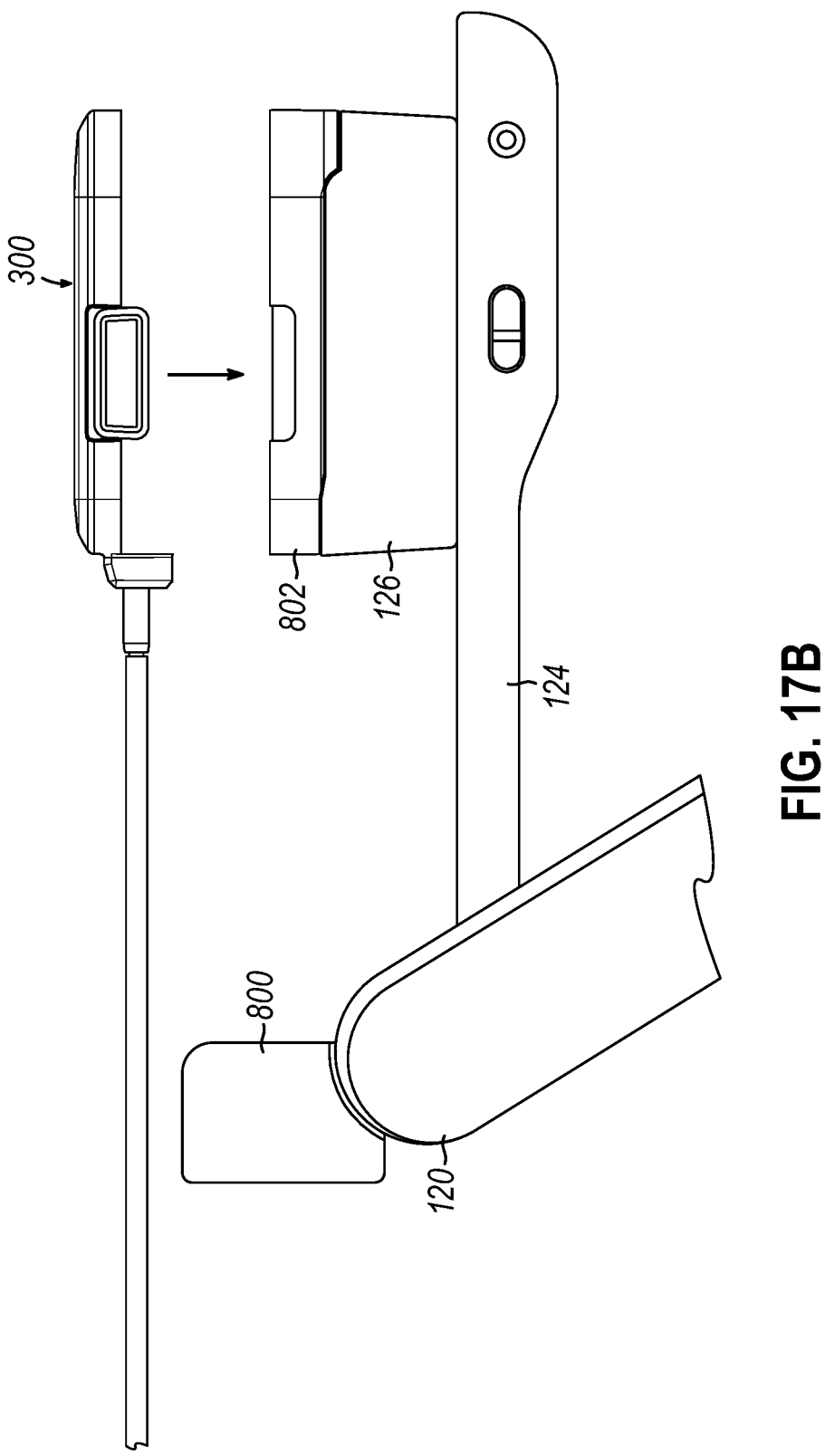
FIG. 17B depicts an elevational side view of the adapter bodies of FIG. 17A, while coupled to the robotic arm of FIG. 2, being initially coupled to the uterine manipulator of FIG. 3.
Figure 17C:
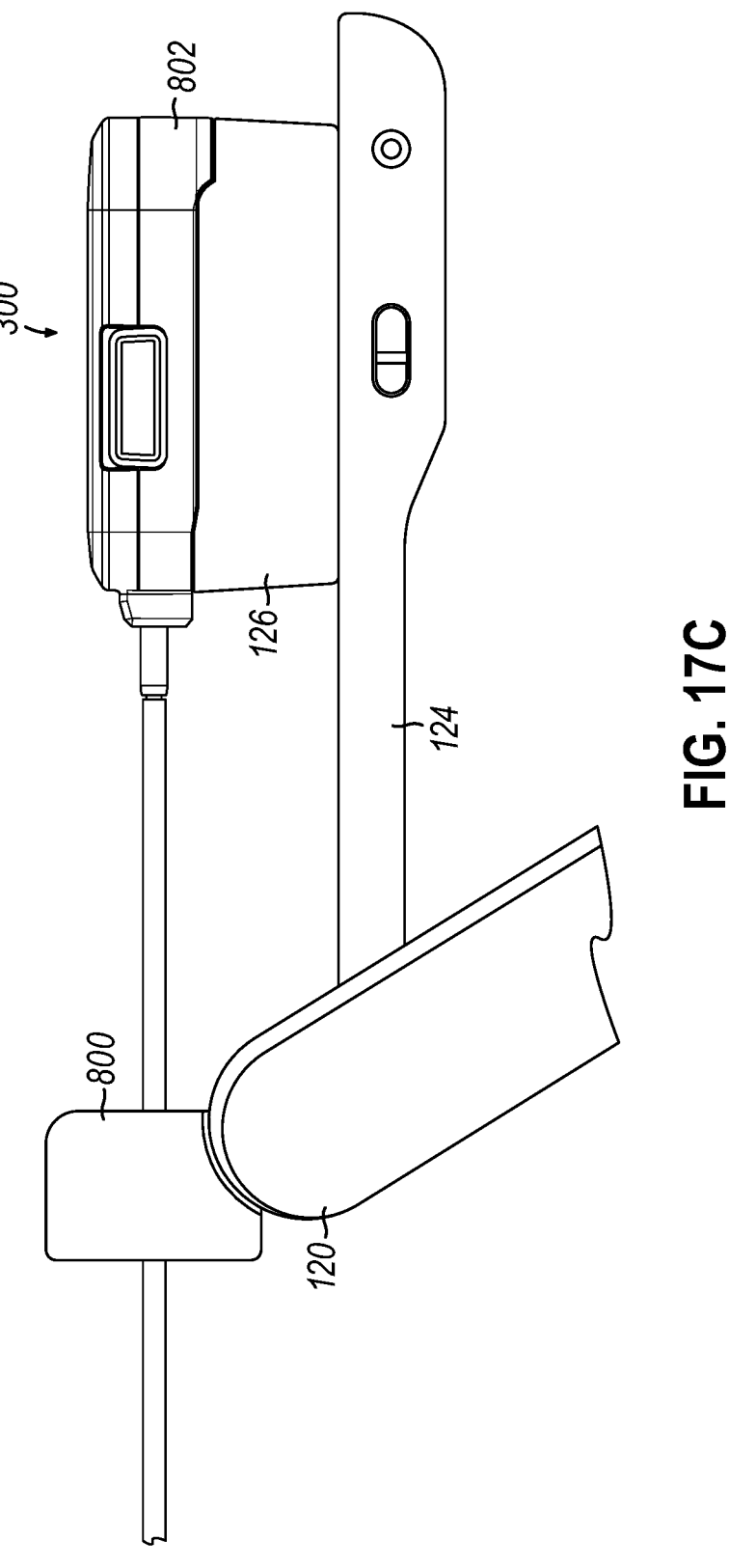
FIG. 17C depicts an elevational side view of the adapter bodies of FIG. 17A coupling the uterine manipulator of FIG. 3 with the robotic arm of FIG. 2.

FIGS. 17A-17C show an illustrative means of coupling uterine manipulator (300) to robotic arm (110) utilizing a cannula adapter body (800) and a tool driver interface adapter body (802). Adapter bodies (800, 802) may be utilized in order to suitably couple a uterine manipulator (300) with a robotic arm (110) for use in accordance with the description herein. In some instances, robotic arm (100) and/or uterine manipulator (300) may be preconfigured for coupling with each other. However, in other instances, one or more adapter bodies (800, 802) may be required.

First, as shown in FIG. 17A, a cannula adapter body (800) may be attached to cannula mount (120) via vertical movement of cannula adapter body (800) onto cannula mount (120). It should be understood that any other suitable coupling movement may be utilized. Cannula adapter body (800) is configured to suitably couple cannula mount (120) with a suitable portion of uterine manipulator (300, 400, 500, 600, 700), such as shaft (320, 420, 520, 620, 720). Additionally, tool driver interface adapter body (802) may be attached to carriage (126) via longitudinal movement. It should be understood that any other suitable coupling movement may be utilized. With adapter bodies (800, 802) suitably coupled to robotic arm (110), as shown in FIG. 17B, uterine manipulator (300) may be attached to robotic arm (110) via adapter bodies (800, 802) by being suitably aligned and translated onto adapter bodies (800, 802). Adapter bodies (800, 802) and/or uterine manipulator (300) may include any suitable components for fast and easy coupling. Such components will be apparent to one skilled in the art in view of the teachings herein.

Next, as shown in FIG. 17C, with uterine manipulator (300) suitably attached to adapter bodies (800, 802), robotic arm (110) may now suitably control uterine manipulator (300) in accordance with the description herein. As mentioned above, while adapter bodies (800, 802) are used in the current example, any other suitable components may be used as would be apparent to one skilled in the art in view of the teachings herein.

Figure 18A:
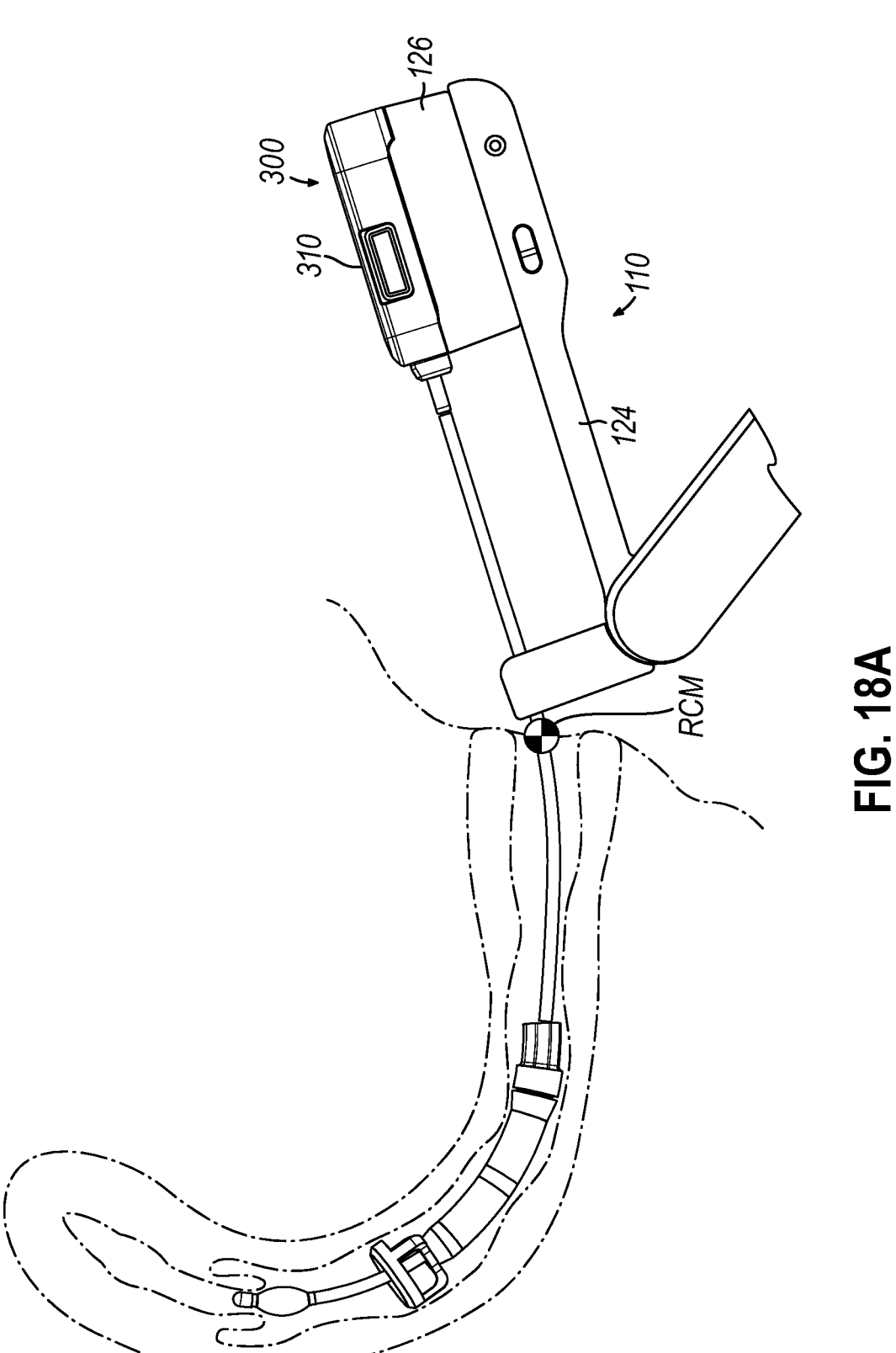
FIG. 18A depicts an elevational side view of the robotic arm of FIG. 2 coupled to the uterine manipulator of FIG. 3 in a proximal position.
Figure 18B:
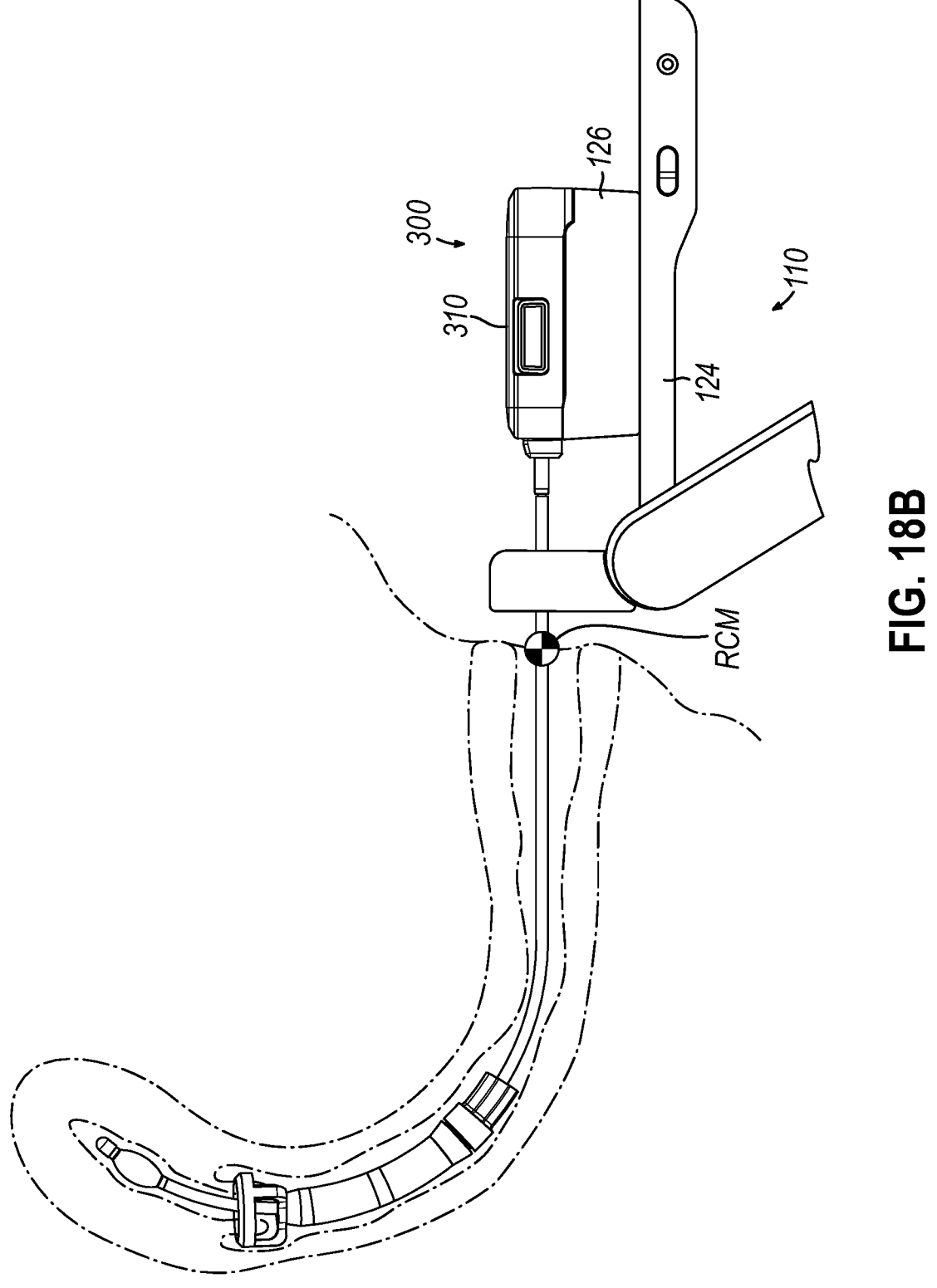
FIG. 18B depicts an elevational side view of the robotic arm of FIG. 2 coupled to the uterine manipulator of FIG. 3, where the robotic arm has actuated the uterine manipulator along an RCM into a distal position.

FIGS. 18A-18B show an illustrative use of robotic arm (100) utilizing an RCM to control uterine manipulator (300) in accordance with the description herein. As shown between FIGS. 18A-18B, robotic arm (100) pivot multiple links (116) about respective joints (118) while also translating carriage (126) and tool driver interface (310) in order to actuate uterine manipulator (300) along an arcuate path, while ensuring that a portion of uterine manipulator (300) remains positioned at the RCM throughout the movement, to thereby suitably place uterine manipulator (300) within the patient in accordance with the description herein. It should be understood that in some instances, carriage (126) may not translate longitudinally along stage (124), such that links (116) and joints (118) primarily actuate uterine manipulator (300) in accordance with the description herein.

Figure 19A:
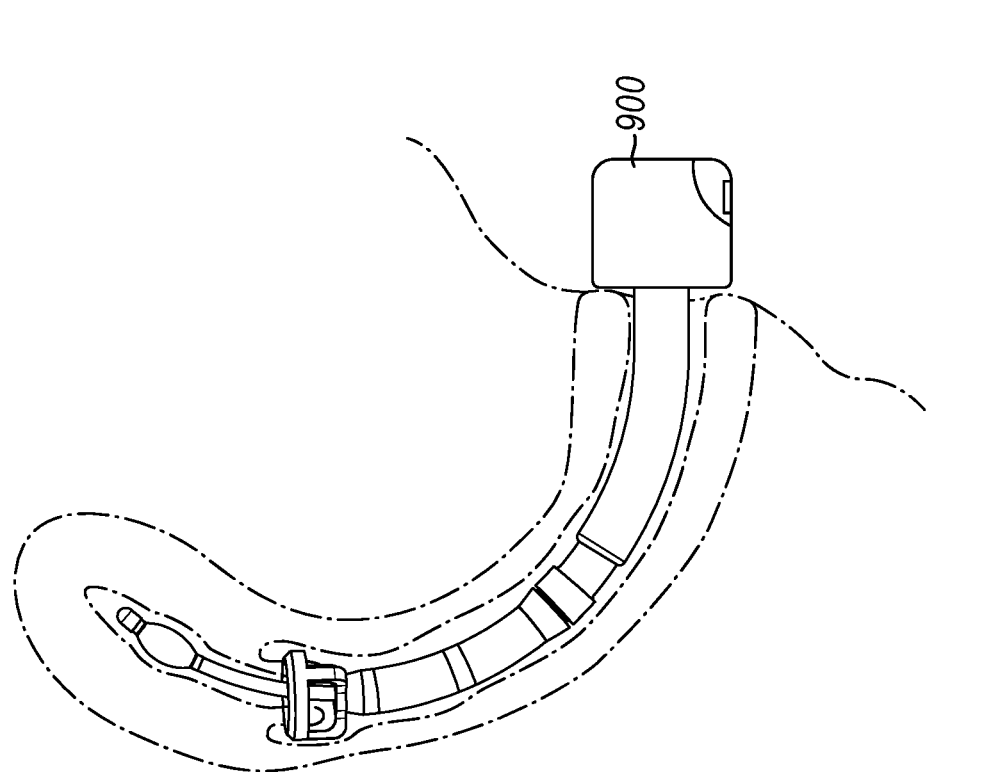
FIG. 19A depicts an elevational side view of a modular uterine manipulator having an adapter body.
Figure 19A:
Figure 19B:
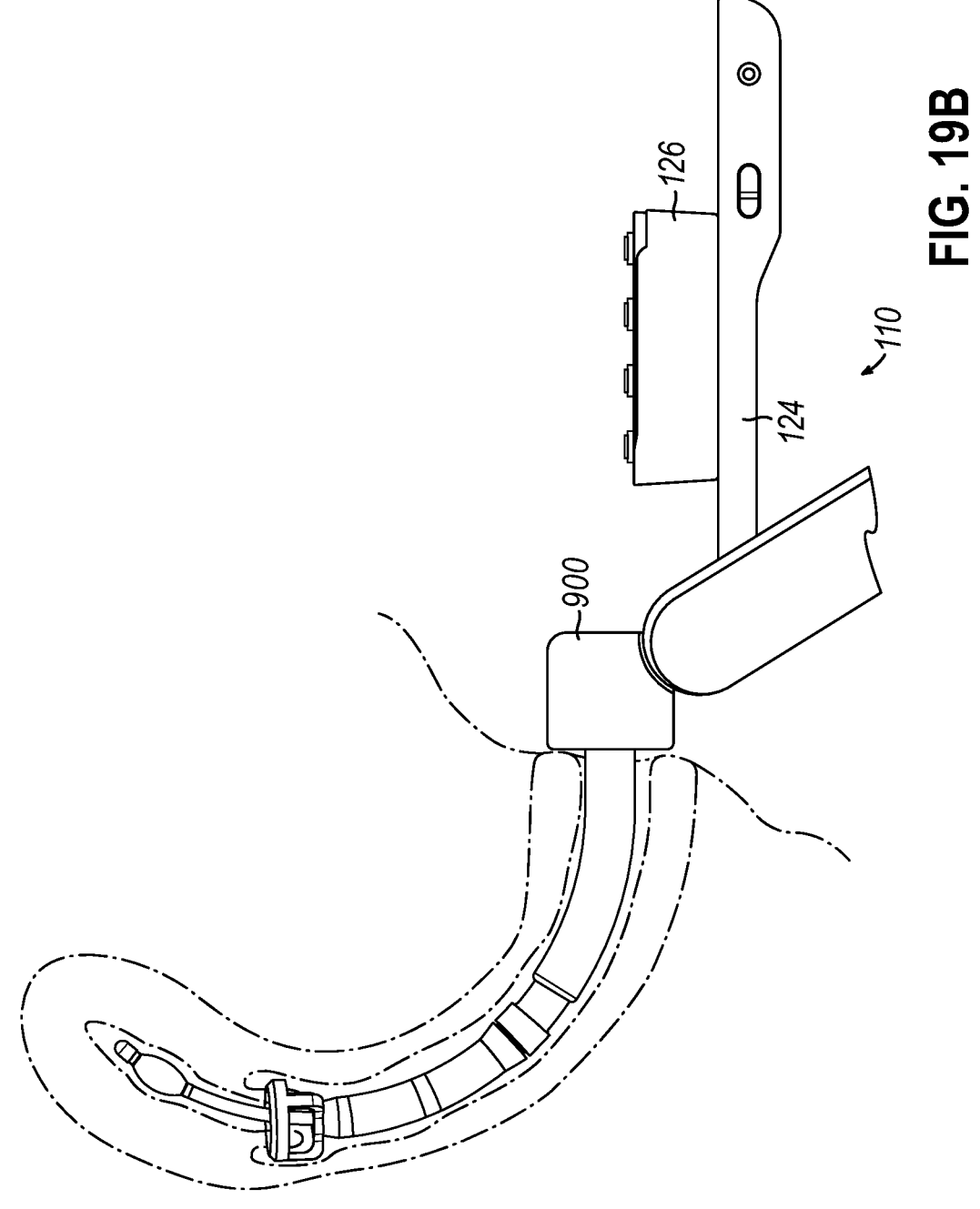
FIG. 19B depicts an elevational side view of a modular uterine manipulator having an adapter body, where the adapter body is coupled to a robotic arm.

In some instances, as shown in FIG. 19A-19B, an adapter body (900) may come pre-attached to a uterine manipulator or suitable components of such a manipular (such as the shaft, sleeve, base, etc.). In such instances, once the uterine manipulator is suitably placed within patient (as shown in FIG. 19A), robotic arm (110) may then be coupled to uterine manipulator by attaching to the adapter body (900).

V. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a robotic coupling base configured to selectively coupled with a robotic arm of a robotic surgical system; (b) a shaft extending distally from the robotic coupling base, the shaft comprising a distal portion dimensioned to be inserted into a naturally occurring orifice of a patient; and (c) a remote center of motion (RCM) measuring feature associated with the robotic coupling base or the shaft, the RCM measuring feature being configured to communicate with the robotic surgical system while the robotic coupling based is selectively coupled with the robotic arm, the RCM measuring feature being configured to measure a distance between an entry point of the naturally occurring orifice of the patient and a predetermined location of the apparatus, the RCM measuring feature being further configured to communicate the distance to the robotic sur-gical system.

Example 2

The apparatus of Example 1, the RCM measuring feature further comprising a contact paddle configured to directly engage anatomical structures adjacent to the naturally occur-ring orifice.

Example 3

The apparatus of Example 2, the contact paddle being slidably coupled to the shaft, the RCM measuring feature further comprising a rotary drive associated with the robotic coupling base, the rotary drive being configured to drive actuation of the contact paddle relative to the shaft.

Example 4

The apparatus of Example 3, the RCM measuring feature being further configured to communicate the distance to the robotic surgical system based on a location of the contact paddle.

Example 5

The apparatus of Example 4, the location of the contact paddle being determinable based on an angular displacement of the rotary drive.

Example 6

The apparatus of any of Examples 1 through 5, the RCM measuring feature comprising an optical measuring sensor.

Example 7

The apparatus of Example 6, the optical measuring sensor being fixed to the robotic coupling base.

Example 8

The apparatus of any of Examples 1 through 7, the RCM measuring feature comprising an extendable measuring body retractably coupled to the robotic coupling base.

Example 9

The apparatus of Example 8, the extendable measuring body being biased toward a proximal position.

Example 10

The apparatus of any of Examples 1 through 9, the shaft comprising a distal anchoring balloon and a colpotomy cup, the colpotomy cup being configured to slide relative to the distal anchoring balloon.

Example 11

The apparatus of Example 10, the shaft comprising a sleeve fixed to the colpotomy cup.

Example 12

The apparatus of Example 11, the shaft comprising a rotary lock configured to selectively fix the location of the sleeve relative to the distal anchoring balloon.

Example 13

The apparatus of any of Examples 1 through 12, the shaft comprising a linear portion and a curved portion, the linear portion extending from the robotic coupling base, the curved portion extending distally from the linear portion.

Example 14

The apparatus of any of Examples 1 through 13, the robotic coupling base being configured to establish fluid communication with a fluid source.

Example 15

The apparatus of Example 14, further comprising an anchoring balloon and a fluid sealing balloon configured to be inflated by the fluid source.

Example 16

An apparatus, comprising: (a) a robotic coupling base configured to selectively couple with a robotic arm of a robotic surgical system; (b) a shaft extending distally from the robotic coupling base, the shaft comprising a distal portion dimensioned to be inserted into a naturally occurring orifice of a patient; and (c) a remote center of motion (RCM) measuring feature, the RCM measuring feature comprising a force detection sensor attached to the robotic arm, the force detection sensor being configured to communicate with the robotic surgical system, the RCM measuring feature being configured to measure a force detected by contacting an anatomical structure adjacent to the naturally occurring orifice of the patient and communicate that contact to the robotic surgical system for use in determining an RCM.

Example 17

The apparatus of Example 16, the RCM measuring feature comprising a cannula mount configured to receive the shaft.

Example 18

The apparatus of Example 17, the force detection sensor being attached to the cannula mount and being distally presented.

Example 19

The apparatus of Example 18, the cannula mount being fixed to the robotic arm.

Example 20

An apparatus, comprising: (a) a robotic coupling base configured to selectively coupled with a robotic arm of a robotic surgical system; (b) a shaft extending distally from the robotic coupling base, the shaft comprising an anchoring assembly dimensioned to be inserted into a naturally occurring orifice of a patient; and (c) a remote center of motion (RCM) measuring feature, the RCM measuring feature being configured to communicate with the robotic surgical system while the robotic coupling base is selectively coupled with the robotic arm, the RCM measuring feature being configured to communicate data to the robotic surgical system for use in determining an RCM.

VI. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components.

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those skilled in the art.

While the examples herein are described mainly in the context of uterine manipulator instruments, it should be understood that various teachings herein may be readily applied to a variety of other types of devices. By way of example only, the various teachings herein may be readily applied to other types of surgical instruments including tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those skilled in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a robotic coupling base configured to selectively couple with a robotic arm of a robotic surgical system;
   (b) a shaft extending distally from the robotic coupling base, the shaft comprising a distal portion dimensioned to be inserted into a naturally occurring orifice of a patient; and
   (c) a remote center of motion (RCM) measuring feature associated with the robotic coupling base or the shaft, the RCM measuring feature being configured to communicate with the robotic surgical system while the robotic coupling base is selectively coupled with the robotic arm, the RCM measuring feature being configured to measure a distance between an entry point of the naturally occurring orifice of the patient and a predetermined location of the apparatus, the RCM measuring feature being further configured to communicate the distance to the robotic surgical system.

2. The apparatus of claim 1, the RCM measuring feature further comprising a contact paddle configured to directly engage anatomical structures adjacent to the naturally occurring orifice.

3. The apparatus of claim 2, the contact paddle being slidably coupled to the shaft, the RCM measuring feature further comprising a rotary drive associated with the robotic coupling base, the rotary drive being configured to drive actuation of the contact paddle relative to the shaft.

4. The apparatus of claim 3, the RCM measuring feature being further configured to communicate the distance to the robotic surgical system based on a location of the contact paddle.

5. The apparatus of claim 4, the location of the contact paddle being determinable based on an angular displacement of the rotary drive.

6. The apparatus of claim 1, the RCM measuring feature comprising an optical measuring sensor.

7. The apparatus of claim 6, the optical measuring sensor being fixed to the robotic coupling base.

8. The apparatus of claim 1, the RCM measuring feature comprising an extendable measuring body retractably coupled to the robotic coupling base.

9. The apparatus of claim 8, the extendable measuring body being biased toward a proximal position.

10. The apparatus of claim 1, the shaft comprising a distal anchoring balloon and a colpotomy cup, the colpotomy cup being configured to slide relative to the distal anchoring balloon.

11. The apparatus of claim 10, the shaft comprising a sleeve fixed to the colpotomy cup.

12. The apparatus of claim 11, the shaft comprising a rotary lock configured to selectively fix the location of the sleeve relative to the distal anchoring balloon.

13. The apparatus of claim 1, the shaft comprising a linear portion and a curved portion, the linear portion extending from the robotic coupling base, the curved portion extending distally from the linear portion.

14. The apparatus of claim 1, the robotic coupling base being configured to establish fluid communication with a fluid source.

15. The apparatus of claim 14, further comprising an anchoring balloon and a fluid sealing balloon configured to be inflated by the fluid source.

16. An apparatus, comprising:
   (a) a robotic coupling base configured to selectively couple with a robotic arm of a robotic surgical system;
   (b) a shaft extending distally from the robotic coupling base, the shaft comprising a distal portion dimensioned to be inserted into a naturally occurring orifice of a patient; and
   (c) a remote center of motion (RCM) measuring feature, the RCM measuring feature comprising a force detection sensor attached to the robotic arm, the force detection sensor being configured to communicate with the robotic surgical system, the RCM measuring feature being configured to measure a force detected by contacting an anatomical structure adjacent to the naturally occurring orifice of the patient and communicate that contact to the robotic surgical system for use in determining an RCM.

17. The apparatus of claim 16, the RCM measuring feature comprising a cannula mount configured to receive the shaft.

18. The apparatus of claim 17, the force detection sensor being attached to the cannula mount and being distally presented.

19. The apparatus of claim 18, the cannula mount being fixed to the robotic arm.

20. An apparatus, comprising:
   (a) a robotic coupling base configured to selectively couple with a robotic arm of a robotic surgical system;
   (b) a shaft extending distally from the robotic coupling base, the shaft comprising an anchoring assembly dimensioned to be inserted into a naturally occurring orifice of a patient; and
   (c) a remote center of motion (RCM) measuring feature, the RCM measuring feature being configured to communicate with the robotic surgical system while the robotic coupling base is selectively coupled with the robotic arm, the RCM measuring feature being configured to communicate data to the robotic surgical system for use in determining an RCM,
   wherein the RCM measuring feature includes at least one of:
      (i) a contact paddle slidably coupled to the shaft and configured to directly engage anatomical structures adjacent to the naturally occurring orifice,
      (ii) an optical measuring sensor fixed to the robotic coupling base, or (iii) an extendable measuring body retractably coupled to the robotic coupling base.

* * * * *